United States Patent
Cheng et al.

(10) Patent No.: US 11,561,179 B2
(45) Date of Patent: Jan. 24, 2023

(54) FLUORESCENCE-CODED MID-INFRARED PHOTOTHERMAL MICROSCOPE

(71) Applicant: Trustees of Boston University, Boston, MA (US)

(72) Inventors: Ji-Xin Cheng, Newton, MA (US); Yi Zhang, Boston, MA (US); Cheng Zong, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/466,672

(22) Filed: Sep. 3, 2021

(65) Prior Publication Data

US 2022/0074861 A1    Mar. 10, 2022

Related U.S. Application Data

(60) Provisional application No. 63/074,668, filed on Sep. 4, 2020.

(51) Int. Cl.
| | | |
|---|---|---|
| *G01N 21/64* | (2006.01) | |
| *G01N 33/50* | (2006.01) | |
| *C12Q 1/04* | (2006.01) | |
| *G01N 21/65* | (2006.01) | |

(52) U.S. Cl.
CPC ........... *G01N 21/6458* (2013.01); *C12Q 1/04* (2013.01); *G01N 21/6428* (2013.01); *G01N 33/5044* (2013.01); *G01N 2021/6439* (2013.01); *G01N 2021/655* (2013.01)

(58) Field of Classification Search
CPC .................................................. G01N 21/6458
See application file for complete search history.

(56) References Cited

U.S. PATENT DOCUMENTS

| | | |
|---|---|---|
| 2007/0021670 A1 | 1/2007 | Mandelis |
| 2018/0052186 A1 | 2/2018 | Su |
| 2018/0259553 A1 | 9/2018 | Yang |
| 2018/0361379 A1 | 12/2018 | Biro |
| 2019/0120753 A1 | 4/2019 | Prater |
| 2019/0187061 A1 | 6/2019 | Han |
| 2019/0293915 A1 | 9/2019 | McCluskey |
| 2020/0073103 A1 | 3/2020 | Wang |
| 2022/0018773 A1 | 1/2022 | Prater |

FOREIGN PATENT DOCUMENTS

WO    WO-2013078471 A1 *    5/2013    ........... G01N 21/171

OTHER PUBLICATIONS

Thor et al., Central laser facility annual report, 2007/2008, p. 164-168.*
Miller et al., Anal Bioanal Chem., 2007, 387: 1705-1715.*
International Search Report and Written Opinion for International Application No. PCT/US2021/049086 dated Nov. 30, 2021.

* cited by examiner

*Primary Examiner* — Bin Shen
(74) *Attorney, Agent, or Firm* — Burns & Levinson LLP; Steven M. Mills

(57) ABSTRACT

Microscopic analysis of a sample includes a fluorescent dye disposed within the sample. A mid-IR optical source generates a mid-infrared beam, which is directed onto the sample to induce a temperature change by absorption of the mid-infrared beam. An optical source generates a probe beam directed to impinge on the sample. A detector detects fluorescent emissions from the sample when the probe beam impinges on the sample. A data acquisition and processing system acquires and processes the detected fluorescent emissions from the sample to: (i) generate a signal indicative of infrared absorption by the sample, (ii) generate a signal indicative of temperature in the sample based on the signal indicative of infrared absorption by the sample, (iii) generate an image of the sample using the signal indicative of temperature in the sample.

11 Claims, 16 Drawing Sheets

(10 of 16 Drawing Sheet(s) Filed in Color)

Fluorescence
FE-MIP 1452 $cm^{-1}$
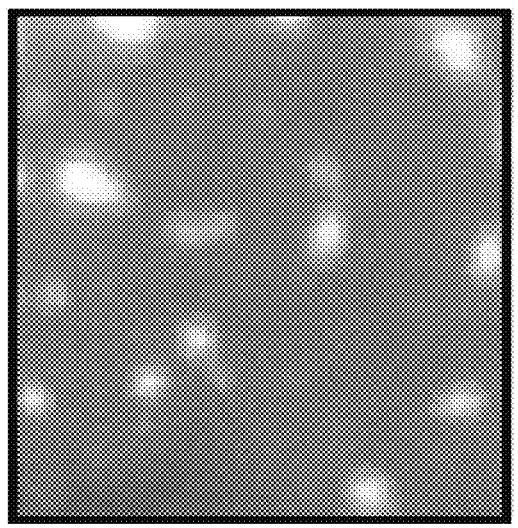 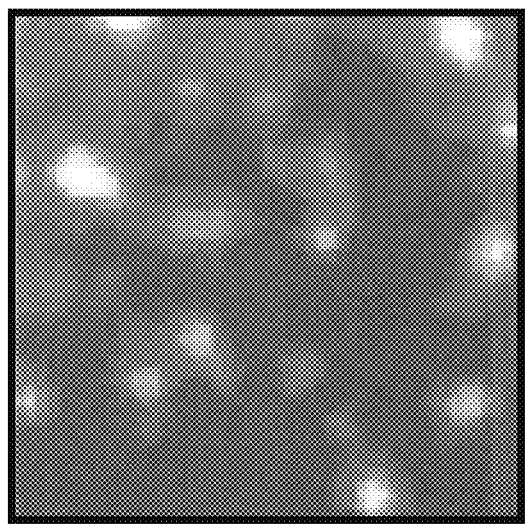
200 nm PS beads
*Fig. 4C*    *Fig. 4D*

Fig. 5A
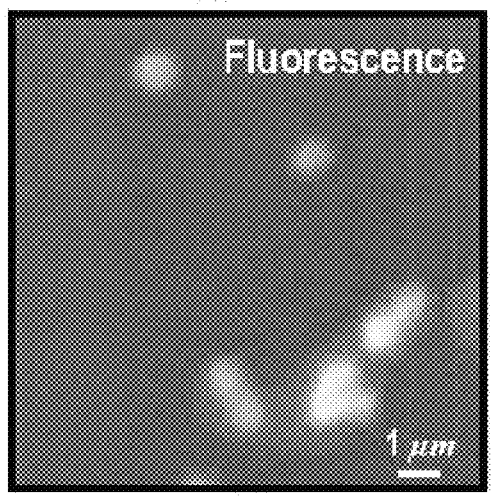
Fig. 5B
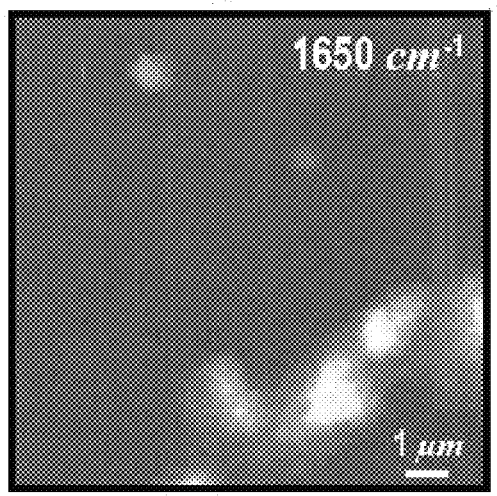
Fig. 5C
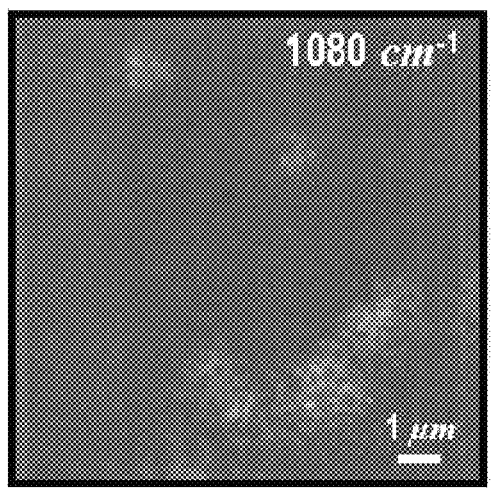
Fig. 5D
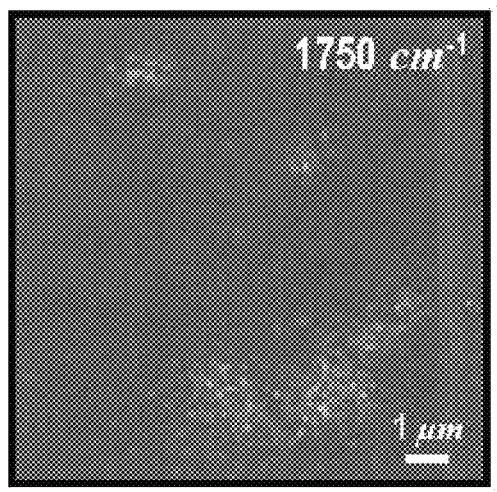
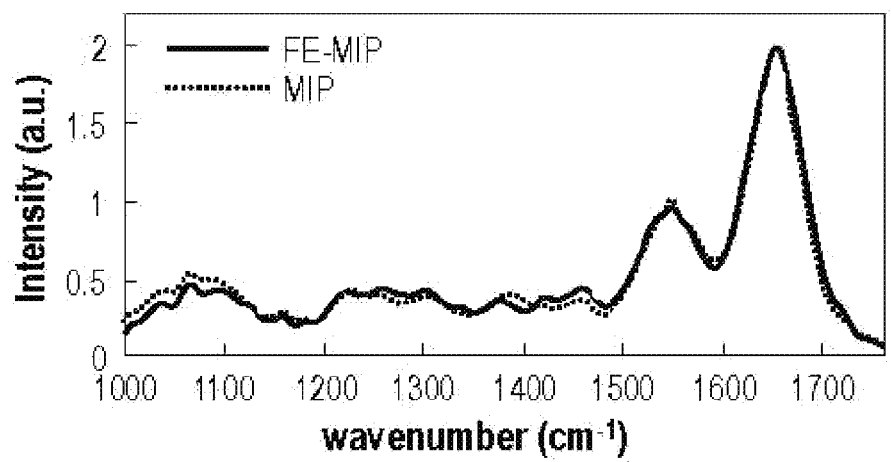
Fig. 5E

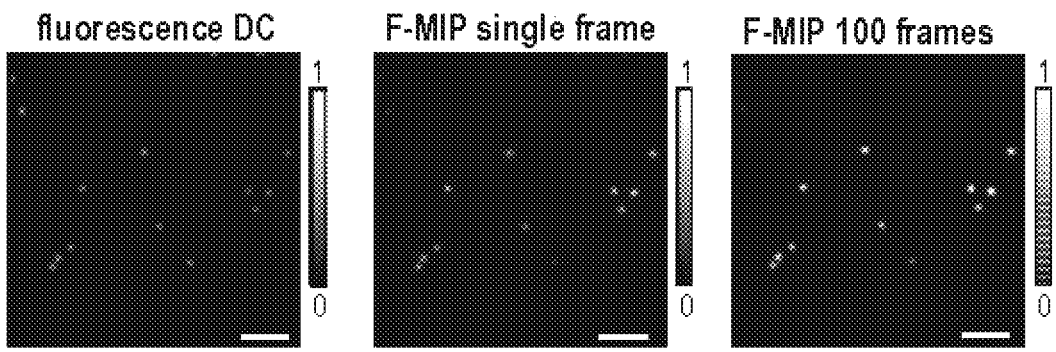
Fig. 11A fluorescence DC  Fig. 11B F-MIP single frame  Fig. 11C F-MIP 100 frames
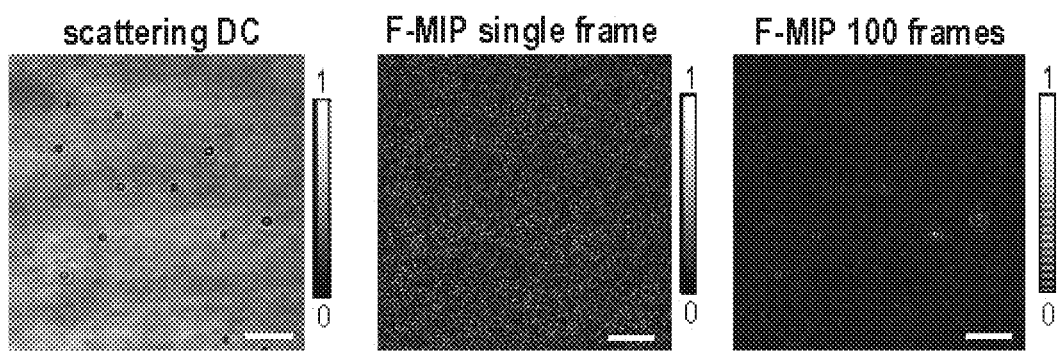
Fig. 11D scattering DC  Fig. 11E F-MIP single frame  Fig. 11F F-MIP 100 frames
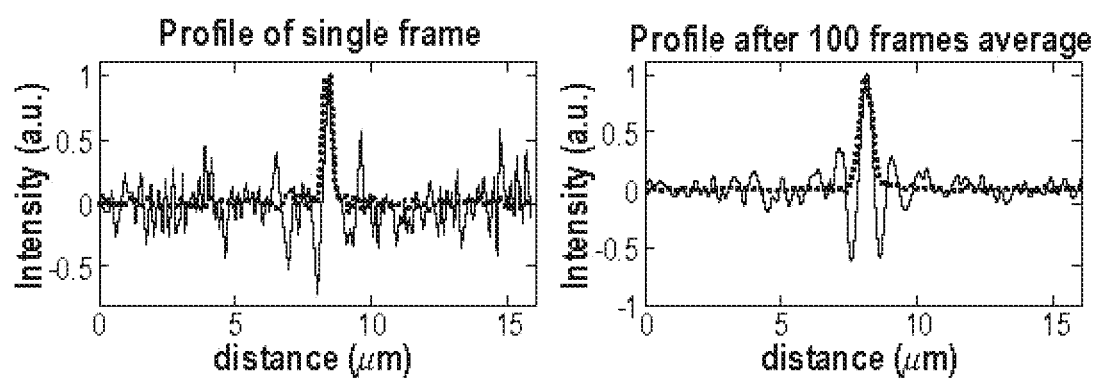
Fig. 11G Profile of single frame  Fig. 11H Profile after 100 frames average

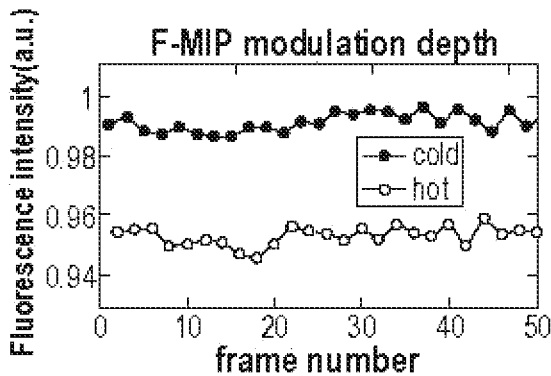
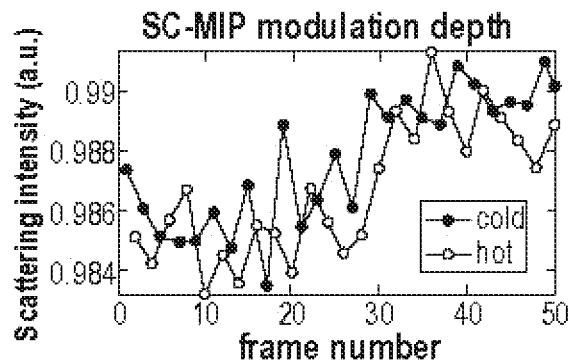
Fig. 11I  Fig. 11J
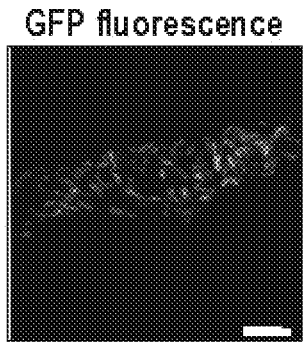 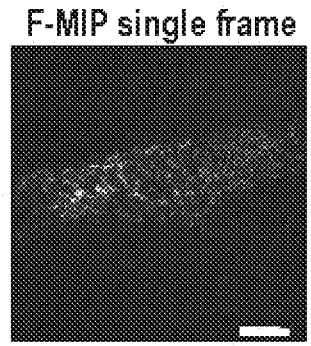 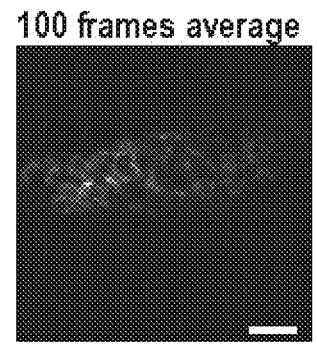
Fig. 11K  Fig. 11L  Fig. 11M
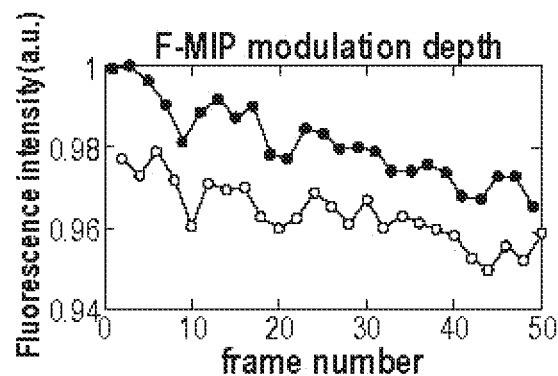
Fig. 11N

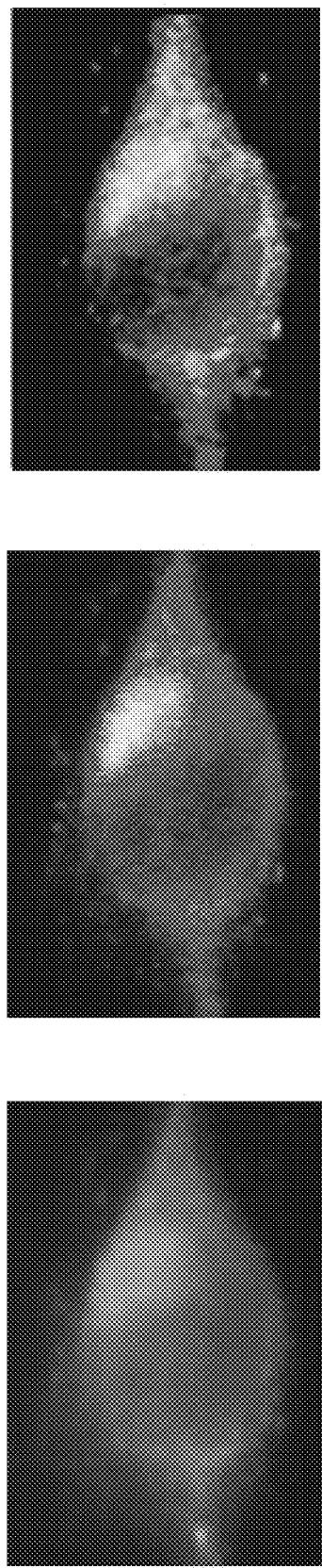
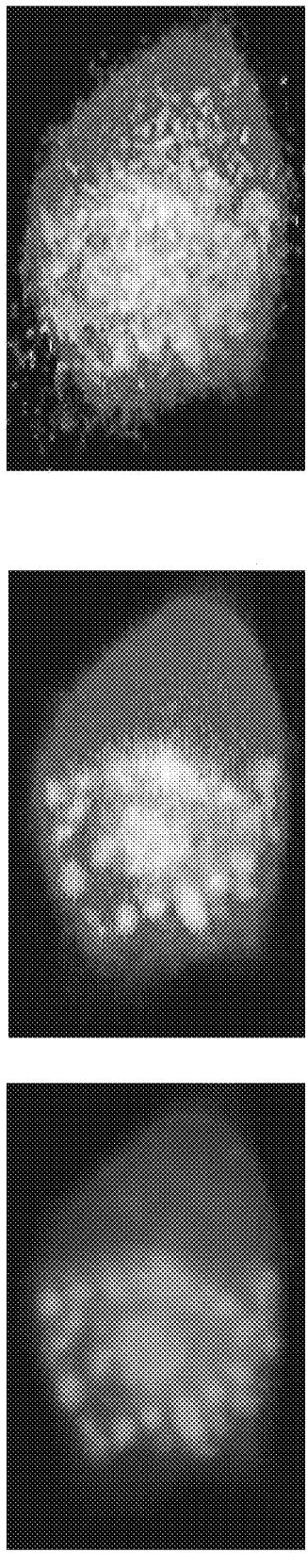

FLUORESCENCE-CODED MID-INFRARED PHOTOTHERMAL MICROSCOPE

CROSS-REFERENCE TO RELATED APPLICATIONS

The present application is related to and claims the benefit of U.S. Provisional Application No. 63/074,668, filed on Sep. 4, 2020, the entire contents of which are incorporated herein by reference.

GOVERNMENT SUPPORT

This invention was made with Government Support under Contract No. GM126049 awarded by the National Institutes of Health. The Government has certain rights in the invention.

BACKGROUND

1. Technical Field

The present disclosure is related to mid_infrared (IR) photothermal (MIP) imaging and, in particular, to a system and method for MIP imaging using a thermally sensitive fluorescent dye to sense temperature increase in a sample induced by mid-infrared absorption.

2. Discussion of Related Art

MW imaging is an emerging technique in which a beam of visible light is used to sense the photothermal lensing effect induced by infrared absorption of molecules. This technology generally provides sub-micron spatial resolution defined by the visible probe beam. Yet, the photothermal lensing effect is a weak effect for most materials. For example, the diffraction coefficient of poly (methyl methacrylate) (PMMA) changes approximately 0.1% per Kelvin. With such low sensitivity to temperature variation, measurements with high spatial resolution cannot be obtained.

SUMMARY

According to one aspect, a system for microscopic analysis of a sample is provided. A fluorescent dye is disposed within the sample. A mid-infrared (IR) optical source generates a mid-infrared beam, the mid-infrared beam being directed onto at least a portion of the sample to induce a temperature change in the portion of the sample by absorption of the mid-infrared beam. An optical source generates a probe beam, the probe beam being directed to impinge on the sample. A detector detects fluorescent emissions from the sample when the probe beam impinges on the sample. A data acquisition and processing system acquires and processes the detected fluorescent emissions from the sample to: (i) generate a signal indicative of infrared absorption by the portion of the sample, (ii) generate a signal indicative of temperature in the portion of the sample based on the signal indicative of infrared absorption by the portion of the sample, (iii) generate an image of the portion of the sample using the signal indicative of temperature in the portion of the sample.

In some exemplary embodiments, the fluorescent dye comprises at least one of rhodamine B, fluorescein, cy2, cy3, Nile red and green fluorescent protein.

In some exemplary embodiments, the mid-infrared beam is a pulse-modulated beam. A pulse repetition frequency of pulses in the mid-infrared beam can be in a range of 1.0 to 1,000 kHz and can nominally be 100 kHz. An on-time of a pulse of the mid-infrared beam can be in a range of 1.0 nanosecond to 1.0 millisecond and in some embodiments can nominally be between 50 and 1000 nanoseconds. A duty cycle of the mid-infrared beam can be in a range of 0.01% to 50% and in some embodiments can be between 1 and 10%.

In some exemplary embodiments, the mid-infrared beam is scanned over a plurality of portions of the sample such that the image is generated for a plurality of portions of the sample.

In some exemplary embodiments, the mid-infrared beam is directed onto a plurality of portions of the sample, and the detector comprises a two-dimensional array of detectors such that the image is generated for the plurality of portions of the sample. In some exemplary embodiments, the detector comprises a camera.

In some exemplary embodiments, the system further comprises an objective configured to focus the mid-infrared beam onto the sample.

According to another aspect, a method for microscopic analysis of a sample is provided. The method includes introducing a fluorescent dye within the sample; directing a mid-infrared beam being onto at least a portion of the sample to induce a temperature change in the portion of the sample by absorption of the mid-infrared beam; directing a probe beam to impinge on the sample; detecting fluorescent emissions from the sample when the probe beam impinges on the sample; and receiving and processing the fluorescent emissions from the sample, the processing including: (i) generating a signal indicative of infrared absorption by the portion of the sample, (ii) generating a signal indicative of temperature in the portion of the sample based on the signal indicative of infrared absorption by the portion of the sample, (iii) generating an image of the portion of the sample using the signal indicative of temperature in the portion of the sample.

In some exemplary embodiments, the fluorescent dye comprises at least one of rhodamine B, fluorescein, cy2, cy3, Nile red and green fluorescent protein.

In some exemplary embodiments, the mid-infrared beam is a pulse-modulated beam. A pulse repetition frequency of pulses in the mid-infrared beam can be in a range of 1.0 to 1,000 kHz and can nominally be 100 kHz. An on-time of a pulse of the mid-infrared beam can be in a range of 1.0 nanosecond to 1.0 millisecond and in some embodiments can nominally be between 50 and 1000 nanoseconds. A duty cycle of the mid-infrared beam can be in a range of 0.01% to 50% and in some embodiments can be between 1 and 10%.

In some exemplary embodiments, the mid-infrared beam is scanned over a plurality of portions of the sample such that the image is generated for a plurality of portions of the sample.

In some exemplary embodiments, the mid-infrared beam is directed onto a plurality of portions of the sample, and the detector comprises a two-dimensional array of detectors such that the image is generated for the plurality of portions of the sample. In some exemplary embodiments, the detector comprises a camera.

The patent or application file contains at least one drawing executed in color. Copies of this patent or patent application publication with color drawing(s) will be provided by the Office upon request and payment of the necessary fee. The present disclosure is further described in the detailed description which follows, in reference to the noted plurality of drawings by way of non-limiting examples of embodiments of the present disclosure, in which like reference numerals represent similar parts throughout the several views of the drawings.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings.

FIGS. 4C and 4D illustrate the fluorescence and FE-MIP images of 200 nm polystyrene beads.

FIG. 5A is the fluorescence image obtained for S. aureus bacteria, according to some exemplary embodiments. FIGS. 5B-5D are FE-MIP images of S. aureus at the 1650 cm$^{-1}$, 1080 cm$^{-1}$, and 1750 cm$^{-1}$ IR pump laser wave numbers, corresponding to DNA, protein and lipid, respectively. FIG. 5E is a curve illustrating the FE-MW spectrum and scattering MIP spectrum for S. aureus.

FIGS. 11A-11N illustrate performance comparison between wide field SC-MIP and wide field F-MIP systems.

FIGS. 12A-12F illustrate normalized F-MIPs images exhibiting a more uniform distribution of the signal arising from proteins in regions labeled by dyes.

DETAILED DESCRIPTION

According to the present disclosure, highly sensitive probes are utilized to improve the detection sensitivity in a MIP microscope. According to the technology of the disclosure, a fluorescence-enhanced mid-infrared photothermal (FE MIP) microscope with high sensitivity is provided. Generally, MIP microscopy uses a pump-probe approach in which a mid-infrared light vibrationally excites a sample, and a visible light probes the resulting thermal effect. Instead of measuring the scattering modulated by mid-infrared absorption as is commonly done in conventional MIP microscopy, according to the present disclosure, a thermally sensitive fluorescent dye is deployed in the sample as the probe, and the modulated fluorescence intensity is measured. According to the exemplary embodiments, the modulated fluorescence intensity can be measured in both a confocal mode and a wide field mode. The result is high imaging sensitivity and component specificity through fluorescence labeling.

Chemical imaging plays an increasingly important role in studying biological systems. It combines molecular spectroscopy with high-resolution spatial information to create quantitative images of molecular distributions. The many conventional chemical imaging tools include stimulated Raman scattering microscopy, Fourier Transform infrared (FTIR) spectroscopy, atomic force microscope infrared (AFM-IR) spectroscopy, and transient absorption microscopy. Among these methods, infrared-based imaging approaches are particularly attractive because they can extract molecular-specific information noninvasively and have much larger cross-section, when compared with Raman scattering. Yet, chemical imaging by conventional FTIR is hampered by the intrinsically low spatial resolution on the micron scale. AFM-IR provides nanoscale resolution but is only applicable to extremely flat specimens under ambient conditions. According to the present disclosure, a contact-free, easy to operate, and highly sensitive method for chemical imaging is provided.

Recently developed mid-infrared photothermal (MIP) microscopy greatly improves According to the technology of the present disclosure, the limitations of conventional MIP microscopy are overcome by a fluorescence-enhanced mid-infrared photothermal (FE-MIP, also referred to herein as "F-MIP") microscope. In this system and method of the disclosure, a sample is labeled with a thermos-sensitive dye and the modulation of fluorescence intensity upon pulsed infrared excitation is probed by a PMT.

Figure 1A:
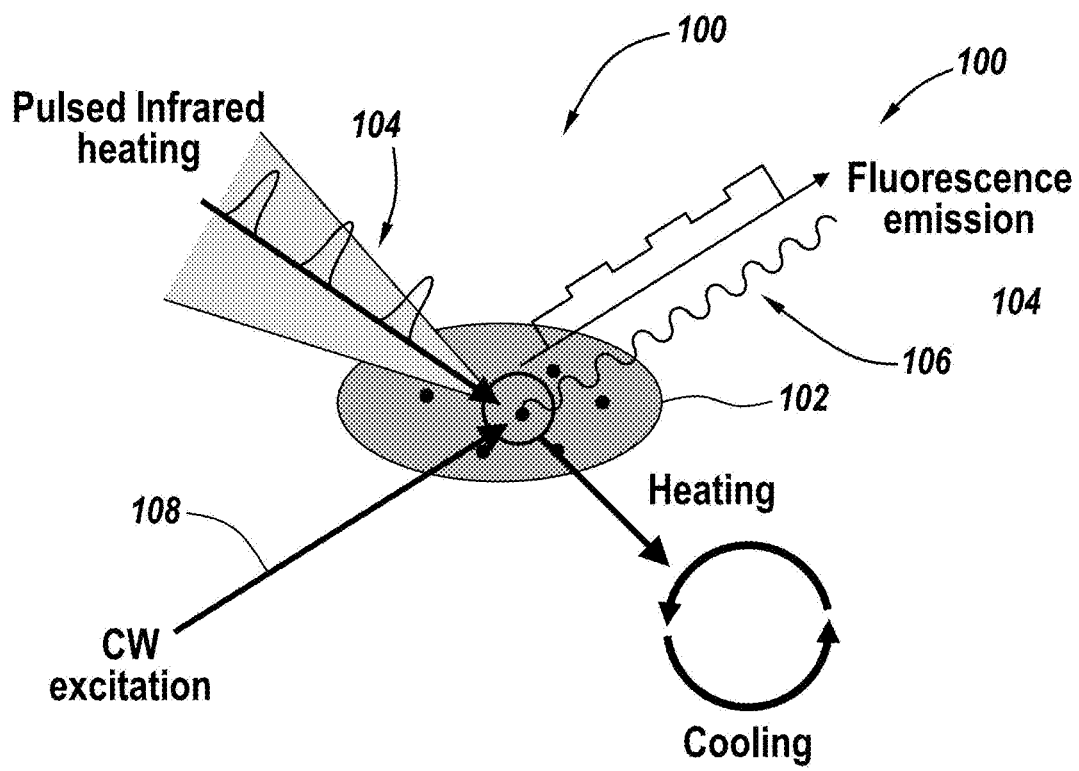
FIG. 1A includes a schematic diagram illustrating operation of a fluorescence-enhanced mid-infrared photothermal microscope, according to some exemplary embodiments.

FIG. 1A includes a schematic diagram illustrating operation of a fluorescence-enhanced mid-infrared photothermal microscope 100, according to some exemplary embodiments. Referring to FIG. 1A, a sample 102 being analyzed includes a fluorescent dye, which, in some particular exemplary embodiments, can be Rhodamine B. A pulse modulated mid-infrared "pump" beam 104 impinges on sample 102. The infrared pulses cause an increase in temperature in the material of sample 102 and a corresponding increase in fluorescence in proximity to the regions of sample 102 illuminated by the infrared pulses. That is, the temperature increase due to infrared absorption changes the molecular structure of the Rhodamine B fluorescent dye and thus change the intensity of the fluorescence induced when sample 102 is illuminated by a continuous wave (CW)

illumination beam 108 of visible light. Hence, fluorescence emission 106, induced by CW illumination beam 108 is modulated by pulsed infrared beam 104. This modulation of the fluorescence is detected and measured such that the modulated temperature change in sample 102 can be analyzed and associated with the sample, such as producing an image of the sample with extremely high resolution and sensitivity. Thus, the FE-MIP of the present disclosure not only takes advantage of the high spatial resolution from MIP, but also harnesses the high sensitivity of certain fluorescent dyes to temperature. The fluorescence label further enables the technology of the disclosure to probe the vibrational spectrum of specific organelles inside a cell.

In some exemplary embodiments, the mid-infrared beam is a pulse-modulated beam. A pulse repetition frequency of pulses in the mid-infrared beam can be in a range of 1.0 to 1,000 kHz and can nominally be 100 kHz. An on-time of a pulse of the mid-infrared beam can be in a range of 1.0 nanosecond to 1.0 millisecond and in some embodiments can nominally be between 50 and 1000 nanoseconds. A duty cycle of the mid-infrared beam can be in a range of 0.01% to 50% and in some embodiments can be between 1 and 10%.

Figure 1B:
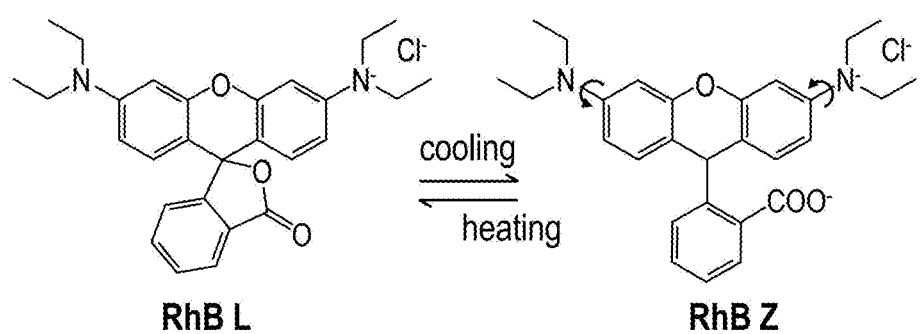
FIG. 1B, which is a schematic diagram illustrating molecular structure change of Rhodamine B caused by heating.

When considering fluorescence as the reporter of temperature rise caused by mid-infrared absorption, according to the present disclosure, the fluorescent molecular thermometers should simultaneously satisfy certain characteristics, namely, high thermal sensitivity, high fluorescence intensity, and robustness on excitation. Such dyes include, for example, rhodamine, fluorescein, cy2, cy3, Nile red, and green fluorescent proteins. In some exemplary embodiments, as noted above, Rhodamine 6G and Rhodamine B are chosen as the fluorescent molecular thermometers, since they exhibit these preferred characteristics. Rhodamine dyes are xanthene derivatives presenting photo-physical properties well suited for a wide range of applications. Rhodamine and its derivatives have long been known for the sensitivity of their fluorescence to temperature. Rhodamine B's fluorescence quantum yield drops with increasing temperature as a consequence of the rotation of diethylamino groups on the xanthene ring, as shown in FIG. 1B, which is a schematic diagram illustrating molecular structure change of Rhodamine B caused by heating. Specifically, FIG. 1B illustrates rotation of diethylamino groups on the xanthene ring of Rhodamine B with changing temperature. The Rhodamine B will change from the zwitterion form of Rhodamine B (RhB Z) to the lactone form RhB L during heating and vice versa.

According to the technology of the present disclosure, using the fluorescence dye as a probe to measure the photothermal effect by the mid-infrared pump can dramatically increase the sensitivity of MIP imaging. The MIP signal contrast is conventionally attributed to temperature-induced changes of local refractive index. The thermally induced refractive index changes in conventional systems led to transient variations of an effective sample/medium light scattering cross-section. Mie scattering theory is used to describe the relation between scattered light and the refractive index. There is a temperature dependence of refractive index for most materials. Taking PMMA as an example, the refractive index changes around 0.02% per Kelvin in temperature between 0 and 80° C. In MIP imaging, the temperature increase induced by the mid-infrared light is around 1 to 5 Kelvin. Thus, the scattering intensity is estimated to change around 0.1% percent per Kelvin. As a comparison, Rhodamine fluorescence intensity has a much larger response to the temperature. Taking Rhodamine B for instance, the fluorescence intensity drops around 2% per Kelvin, which is two orders of magnitude larger than the scattering modulation depth caused by refractive index change.

FE-MIP microscope 100 of the present disclosure provides another benefit for chemical imaging, that is, the ability to record the vibrational spectrum of a specific component in a complex environment. For example, a mammalian cell contains numerous spatially organized organelles. The process of chemically imaging a specific organelle in a complex cellular system is challenging. Thus far, only lipid droplets that are densely packed with C—H bonds have been heavily studied by coherent Raman scattering microscopy. In contrast, fluorescent probes have the ability to specifically label every component in a cell. For example, Rhodamine Phalloidin can attach to the cytoskeleton. Therefore, FE-MIP microscope 100 can obtain an IR spectrum that presents the cytoskeleton chemical information. Collectively, these benefits of FE-MIP microscope 100 provide a highly sensitive and selective chemical imaging of nanoparticles, fingerprinting of bacteria, and vibrational imaging of cytoskeleton in mammalian cells.

Figure 2A:
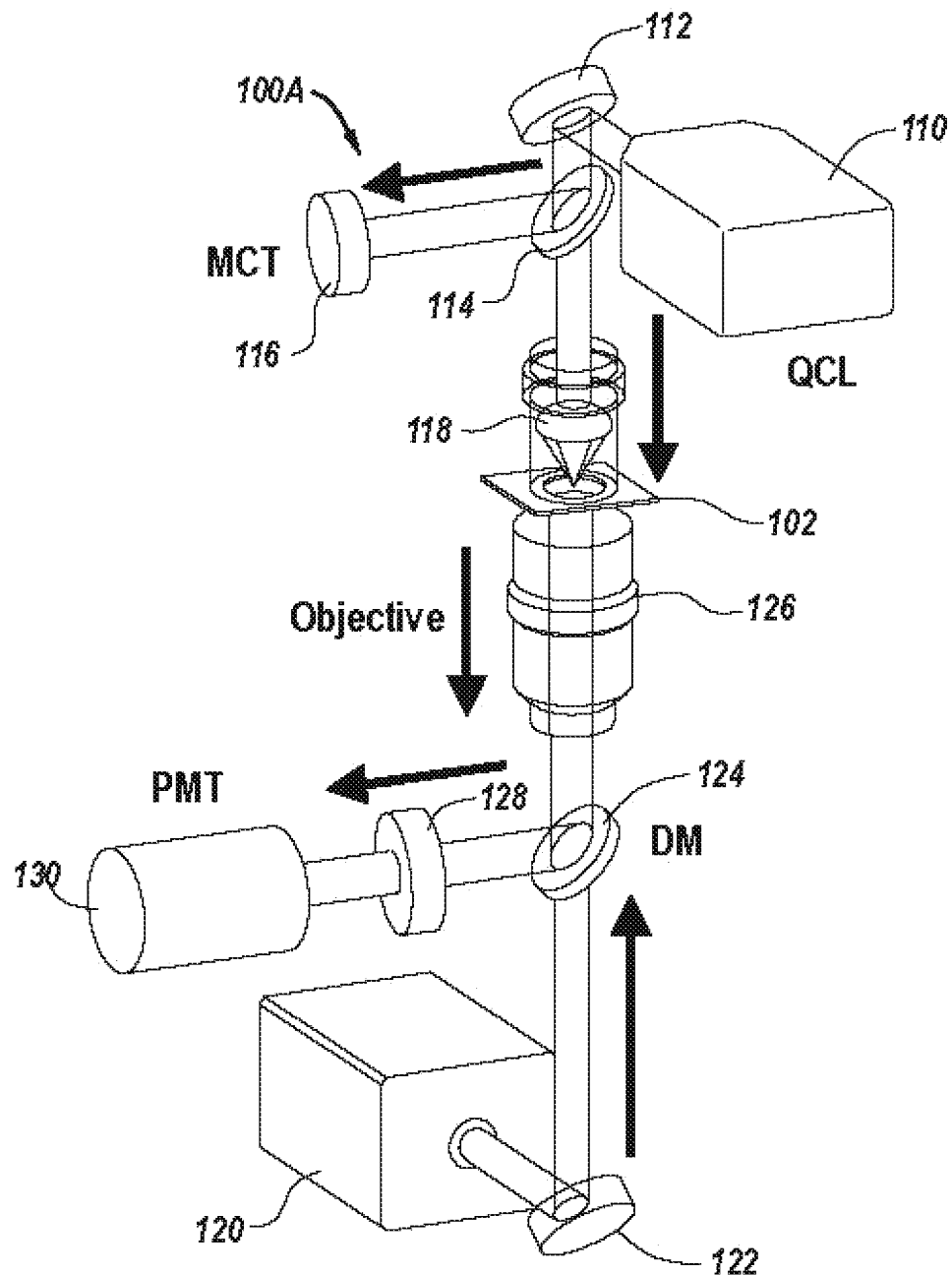
FIG. 2A includes a schematic diagram of a point scanning FE-MIP microscope, according to some exemplary embodiments.
Figure 2B:
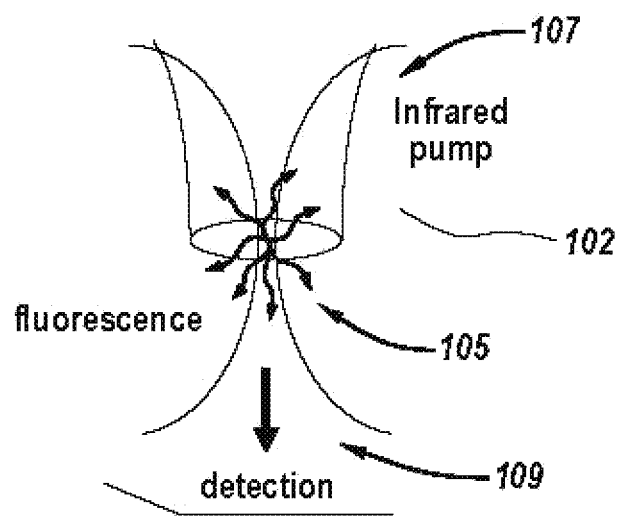
FIG. 2B is a schematic diagram of the effects at the sample being analyzed.

FIG. 2A includes a schematic diagram of a point scanning FE-MIP microscope 100A, according to some exemplary embodiments. FIG. 2B is a schematic diagram of the effects at the sample 102 being analyzed. Referring to FIGS. 2A and 2B, microscope 100A is used to analyze sample 102, which includes a fluorescent dye, which, in some particular exemplary embodiments, can be Rhodamine B. A pulsed mid-infrared pump beam is provided by a quantum cascade laser (QCL) 110 to a reflective optic 112 which reflects the mid-infrared pump beam through a calcium fluoride ($CaF_2$) optic 114 to a reflective objective 118, which focuses the IR pump beam 107 onto controlled locations on sample 102. The IR beam can have a wavenumber in the range of 100 to 4000 $cm^1$. Part of the mid-infrared pump beam is reflected by $CaF_2$ optic 114 to a mercury cadmium telluride (MCT) detector 116, which measures the beam. A CW probe beam at a nominal wavelength of 532 nm is generated and output by source 120 and passes through dichroic mirror 124 and is focused at sample 102 by water immersion objective 126, resulting in fluorescence 105 at sample 102. Dichroic mirror 124 reflects the CW beam returning from sample 102 to photomultiplier tube (PMT) 130, which collects and detects and measures the light, including the effects of the modulated fluorescence from sample 102, as indicated at 109.

Figure 2C:
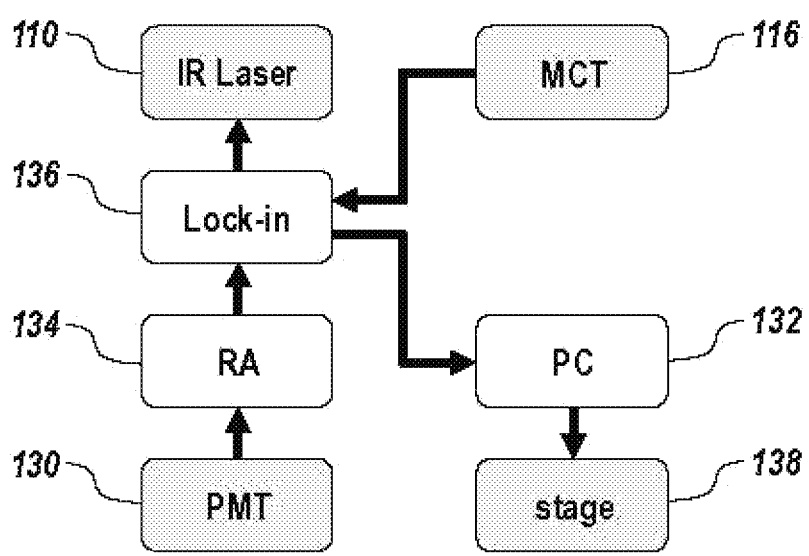
FIG. 2C includes a schematic functional block diagram illustrating components for control and analysis in the FE-MIP microscope, according to some exemplary embodiments.

FIG. 2C includes a schematic functional block diagram illustrating components for control and analysis in the FE-MW microscope, according to some exemplary embodiments. Referring to FIG. 2C, the photothermal signal, which includes the effects of the modulated fluorescence from sample 102, is collected by PMT 130. The signals from PMT 130 are amplified by resonant amplifier 134 and detected by lock-in amplifier 136. All of the system components, including IR laser (QCL) 110, lock-in amplifier 136, resonant amplifier 134, PMT 130, MCT 116 and position stage 138 interface with processor/computer 132, which is used to control positioning of the sample stage 138 and synchronization of IR pump modulation and illumination, as well as data acquisition and analysis.

FIG. 2A illustrates a point scanning configuration of FE-MW microscope 100A.

Continuing to refer to FIGS. 2A through 2C, a pulsed mid-IR pump beam, generated by tunable (from 1000 to 1886 cm-1) quantum cascade laser (QCL) 110, which can be, for example, a MIRcat2400 QCL, manufactured and/or sold by Daylight Solutions, operating at 100 kHz repetition rate, passes through a calcium fluoride ($CaF_2$) cover glass optic 114 and then is focused onto sample 102 through a gold-coating reflective objective lens 118 (for example, 52×; NA, 0.65; Edmund Optics, #66589). Continuous-wave probe laser 120 (for example, Cobolt, Samba 532 nm) beam is focused onto the same spot of sample 102 from the opposite side by a high NA refractive objective 126 (for example, 60×; NA, 1.2; water immersion; Olympus, UPlanSApo). The probe beam is aligned to be collinear to the mid-IR pump beam to ensure the overlap of the two focus to achieve a good signal level. A scanning piezo stage (for example, Mad City Labs, Nano-Bio 2200) with a maximum scanning speed of 200 μs/pixel is used to scan sample 102. The fluorescence excited the by probe laser 120 is then collected by the high NA refractive objective 126 and reflected by dichroic mirror 124 (for example, DMSP550R, 550 nm cutoff, THorlabs). The fluorescence is then filtered by longpass filter 128 (for example, FEL0550, 550 nm cutoff, THorlabs) and collected by PMT 130 (for example, Hamamastsu H10721-110). In the imaging procedure according to the disclosure, sample 102 on a $CaF_2$ cover glass is first localized by the fluorescence signal. Then, the pulsed infrared pump is turned on. The modulated scattering is collected by PMT 130, and the MIP signal is extracted by lock-in amplifier 136, which detects/demodulates the signal to recover the IR modulation signal. Before reflective objective 118, the infrared laser beam passes through a $CaF_2$ slip in optic 114, and the refection of the infrared laser is measured by MCT detector 116 for normalization of IR power at each wavelength.

Figure 3A:
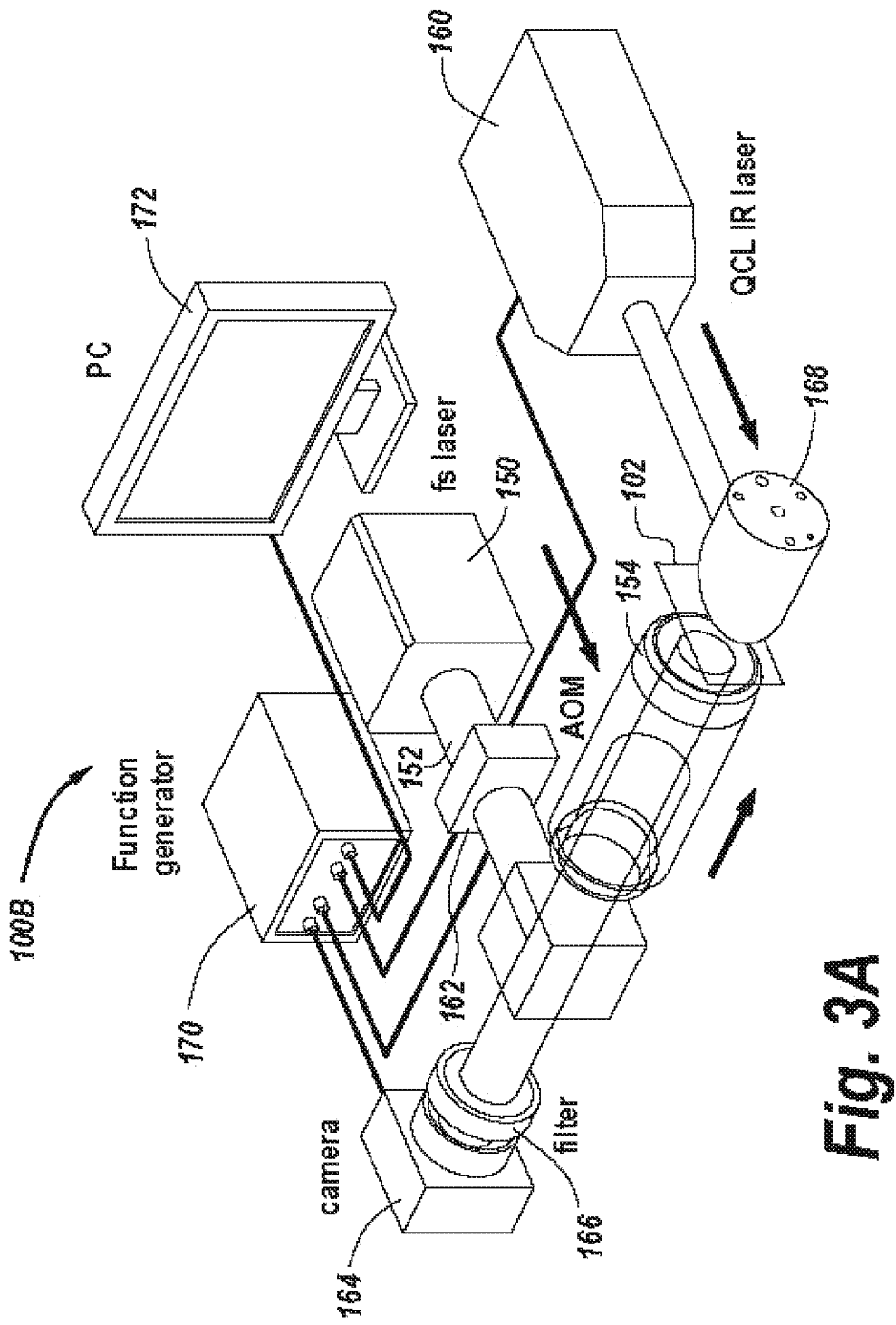
FIG. 3A includes a schematic diagram of a wide-field FE-MW microscope, according to some exemplary embodiments.
Figure 3B:
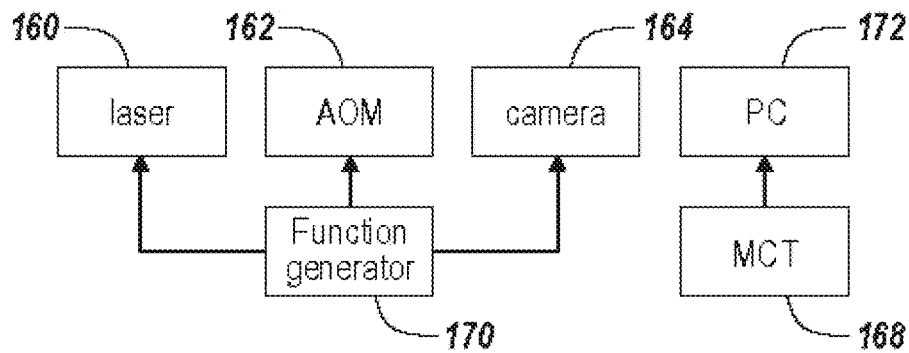
FIG. 3B includes a schematic functional block diagram illustrating components for control and analysis in the FE-MIP microscope of FIG. 3A, according to some exemplary embodiments.

FIG. 3A includes a schematic diagram of a wide-field FE-MW microscope 100B, according to some exemplary embodiments. FIG. 3B includes a schematic functional block diagram illustrating components for control and analysis in the FE-MIP microscope 100B of FIG. 3A, according to some exemplary embodiments. Referring to FIGS. 3A and 3B, a laser 150, for example, a 1040 nm full spectrum laser 150, is used as the CW excitation light source. In some particular exemplary embodiments, laser 150 is double-frequency to 520 nm. This beam is chopped by acousto-optic modulator (AOM) 162 to produce probe beam pulses. The excitation beam 152 is focused on the back aperture of objective 154 to achieve epi illumination. Camera 164 is disposed to collect the fluorescence signal filtered by long pass filter 166, which can be a 520 nm long pass filter. The mid-infrared pulse signal is generated by QCL 160 to heat sample 102 and is synchronized with the frame rate of camera 164. Hot frames and cold frames generated by camera 164 are recorded, hot frames being generated when the IR pump effects are present, and cold frames being generated with they are not present. The difference between the hot and cold frames is used to create a photothermal image.

Continuing to refer to FIGS. 3A and 3B, in some exemplary embodiments, function generator 170 can be used to trigger and synchronize system components, including generation and modulation of the pulsed IR signal by laser 150, the CW illumination signal generated by laser 150, and detection and data acquisition by camera 164. Processor or computer 172 extracts the FE-MW signal and further processes images from camera 164.

In the particular exemplary embodiment illustrated in FIGS. 3A and 3B, the same mid-IR laser source 160 as is used in the embodiment of FIGS. 2A-2C is used to IR-pump sample 102. The pulsed mid-IR pump beam, generated by tunable (for example, from 1000 to 1886 cm-1) quantum cascade laser (QCL) 160 (for example, QCL, Daylight Solutions, MIRcat-2400) operating at 100 kHz repetition rate is focused by a parabolic mirror to illuminate sample 102. A 520 nm femtosecond pulse laser 150 as probe is epi-illuminated on sample 102. The laser 150 focused on the back aperture of objective 154 thus forms even illumination on sample 102. The fluorescence beam is then filtered by 550 nm long pass filter 166 and collected by camera 164 (for example, FLIR Grasshopper3 GS3-U3-32S4M). In some exemplary embodiments, camera 164 is operated at a nominal frame rate of 100 Hz. Half of the total frames are tuned off, and by subtracting the IR-on frame from the IR-off frame, the fluorescence-coded MIP image is obtained.

According to some exemplary embodiments, to prepare bacterial samples for FE-MIP imaging, S. aureus ATCC 6538 can be used as a model strain. Living S. aureus cells are first fixed by 10% formalin solution (Thermo Fisher Scientific), and then centrifuged and washed with phosphate-buffered saline solution. Triton-X solution (Sigma) can be added to permeabilize the cell membrane to facilitate fluorescence staining. Fluorescent labeling can be carried out by incubating bacterial cells with $10^{-4}$ M Rhodamine 6G (Sigma) solution for one hour at room temperature in the dark. After final conjugation and washing steps, bacterial cells can be deposited and dried on a $CaF_2$ coverslip for imaging.

Figure 4A:
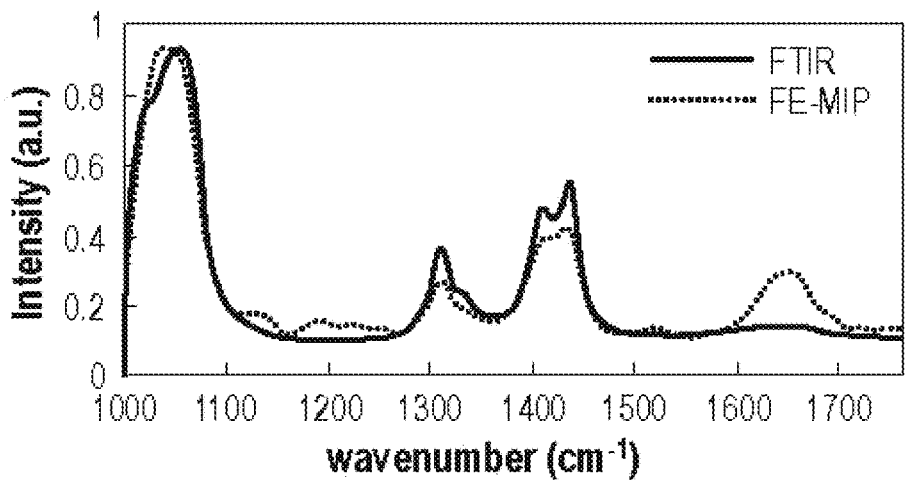
FIG. 4A illustrates the FE-MW and FTIR spectra for DMSO.
Figure 4B:
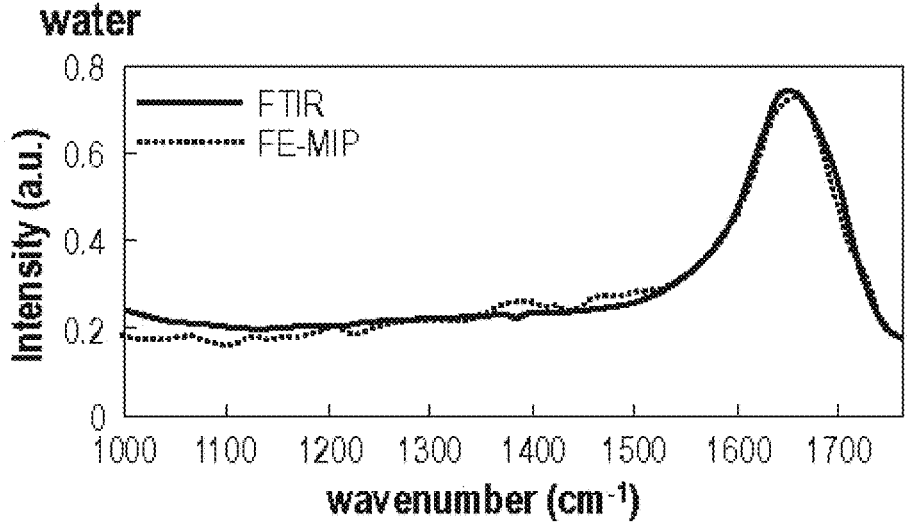
FIG. 4B illustrates the FE-MW and FTIR spectra for water.

According to the present disclosure, the spectral fidelity of the FE-MIP system of the disclosure to measure the mid-infrared spectrum of standard samples is described. As described above, Rhodamine 6G in dimethyl sulfoxide (DMSO) and aqueous solutions as standard samples are chosen. The point scanning embodiment of FIGS. 2A-2C are used, and the FE-MIP spectrum is measured with 0.02 mW excitation power and the mid IR tuning from 1000 to 1750 cm-1. The spectrum scanning speed is 50 cm-1/s. The spectral fidelity is confirmed by comparing the MIP spectra to the Fourier Transform infrared (FTIR) spectra, as shown in FIG. 4A. In FIG. 4A, the FE-MIP spectrum of DMSO is illustrated. The FE-MIP spectrum shows 10 μMol/L R6G DMSO solution with spectrum scanning speed 50 cm-1. The FE-MW spectrum for water is shown in FIG. 4B. The FE-MW spectrum of single 200 nm RhB PS beads, spectrum scanning speed 50 cm-1. FIGS. 4C and 4D illustrate the fluorescence and FE-MIP images of 200 nm beads. Pixel dwell time: 1 ms. Step size: 100 nm; Scale bar: 1 μm.

The sensitivity of FE-MIP is confirmed by mapping 200 nm polystyrene (PS) beads labeled with Rhodamine B dye. The beads are dispersed on a calcium fluoride coverslip. FIGS. 4C and 4D illustrate the fluorescence and FE-MIP images of PS beads with the IR laser tuned to 1450 $cm^{-1}$. To validate the spectral fidelity, an individual bead is analyzed, and the FE-MIP spectrum is recorded in the fingerprint region. The spectrum is consistent with the FTIR spectrum. The scattering-based MIP and FE-MIP are consistent. Yet, under the same power of 16 mW for the IR laser, 30 mW in the probe was used for the scattering-based MIP. In contrast, only 0.02 mW of probe was used for recording the FE-MIP image.

When imaging bio-samples, especially living cells, the phototoxicity must be taken into consideration. Compared with the scattering method, the FE-MIP of the current disclosure is very frugal in photo budget. For the FE-MW method, the power density for the probe beam is around 1 KW/cm^2. While, the scattering MIP uses a probe power density 100 $kW/cm^2$, which is higher than FE-MW by 2-3 orders of magnitude.

The FE-MW microscopy of the present disclosure is applicable to chemical imaging of bacteria. According to some exemplary embodiments, S. aureus was imaged using the point scanning approach according to the embodiments described in detail above in connection with FIGS. 2A-2C. The images obtained are illustrated in FIGS. 5A through 5D. FIG. 5A is the fluorescence image obtained for *S. aureus* bacteria, according to some exemplary embodiments. FIGS. 5B-5D are FE-MIP images of *S. aureus* at the 1650 cm$^{-1}$, 1080 cm$^{-1}$, and 1750 cm$^{-1}$ IR pump laser wave numbers, corresponding to DNA, protein and lipid, respectively. FIG. 5E is a curve illustrating the FE-MW spectrum and scattering MIP spectrum for *S. aureus*. Due to the sensitivity property of the FE-MIP of the present disclosure, far smaller probe intensity is used to image the spectrum of bacteria, which can minimize the phototoxicity.

Figure 6A:
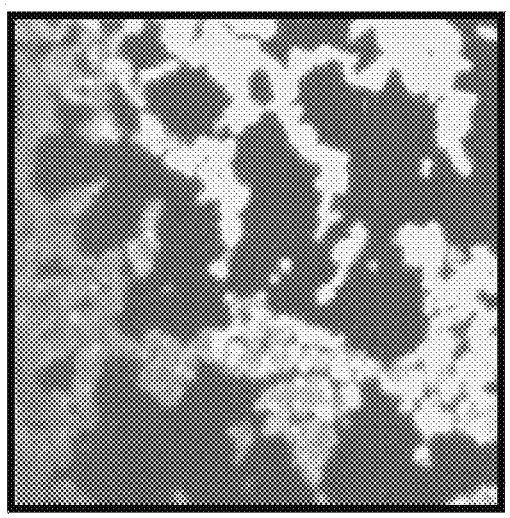
FIG. 6A is the fluorescence image obtained for S. aureus bacteria, according to some exemplary embodiments.
Figure 6B:
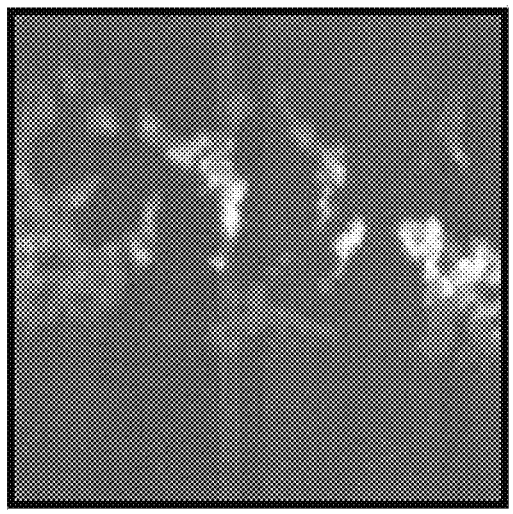
FIGS. 6B-6D are FE-MIP images of S. aureus at the 1650 cm$^{-1}$, 1080 cm$^{-1}$, and 1750 cm$^{-1}$ IR pump laser wave numbers, corresponding to corresponding to protein amide I band, nucleic acid phosphate band, and off-resonance, respectively.
Figure 6C:
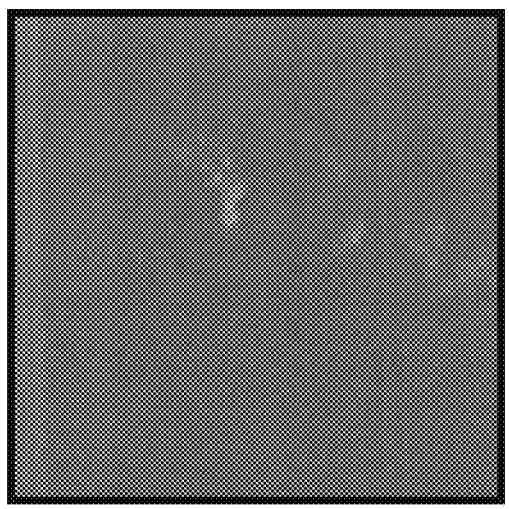
Figure 6D:
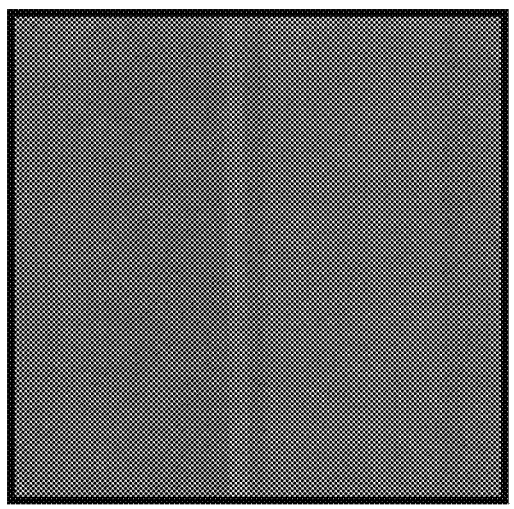

The performance of wide field FE-MW for bacterial imaging, according to the present disclosure, is also verified, as shown in FIGS. 6A through 6D. According to some exemplary embodiments, *S. aureus* was also imaged using the wide field approach according to the embodiments described in detail above in connection with FIGS. 3A-3B. The images obtained are illustrated in FIGS. 6A through 6D. FIG. 6A is the fluorescence image obtained for *S. aureus* bacteria, according to some exemplary embodiments. FIGS. 6B-6D are FE-MIP images of *S. aureus* at the 1650 cm$^{-1}$, 1080 cm$^{-1}$, and 1750 cm$^{-1}$ IR pump laser wave numbers, corresponding to protein amide I band, nucleic acid phosphate band, and off-resonance, respectively.

According to the present disclosure, fluorescence imaging is a sophisticated technique that is applied to FE-MIP to provide important improvements. For example, the illumination microscope can effectively improve the resolution by two times and can be directly applies in the wide field system and realize super resolution chemical imaging. Other super resolution microscope methods, including, for example, stimulated emission depletion (STED) microscope methods can also be applied to the technology described herein.

As described herein, the FE-MIP microscopy of the present disclosure can be applied to take the fingerprint spectrum of the cytoskeleton, which is buried inside the cell. By fluorescent labelling, the cytoskeleton can be located, and its spectrum can be measured. It is noted that the technology is not only applicable to the cytoskeleton. For example, Rhodamine 123 has the ability to label mitochondrion. The green fluorescent protein, which is known for labeling cells, is also thermally sensitive. Thus, the green fluorescence can be applied according to the disclosure to image the chemical information.

Mid-infrared photothermal microscopy according to the present disclosure is a chemical imaging technology in which a visible beam senses the photothermal effect induced by a pulsed infrared laser. This technology provides infrared spectroscopic information at sub-micron spatial resolution and enables infrared spectroscopy and imaging of living cells and organisms. However, current mid-infrared photothermal imaging sensitivity suffers from a weak dependance of scattering on temperature, and the image quality is vulnerable to the speckles caused by scattering. The present disclosure is directed to a novel version of mid-infrared photothermal microscopy in which thermo-sensitive fluorescent probes are used to sense the mid-infrared photothermal effect. According to exemplary embodiments, the fluorescence intensity can be modulated at the level of 1% per Kelvin, which is 100 times larger than the modulation of scattering intensity. In addition, fluorescence emission is free of interference, thus greatly improving the image quality. Moreover, fluorophores can target specific organelles or biomolecules, thus augmenting the specificity of photothermal imaging. Spectral fidelity is confirmed through fingerprinting a single bacterium. Finally, the photobleaching issue, in which the fluorophore molecules are damaged by the visible light, is successfully addressed through the development of the wide-field fluorescence-detected mid-infrared photothermal microscope which allows video rate bond-selective imaging of biological specimens.

Visualizing the molecular composition and monitoring the molecular dynamics in a complex living system is a central theme of life science. Fluorescence microscopy has been widely adopted in biomedical research as it provides high-speed background-free imaging with exquisite molecular specificity and superior resolution reaching the nanometer scale. While fluorescence microscopy excels at mapping the distribution and dynamics of tagged organelles such as mitochondria and biomolecules such as glucose and cholesterol, it does not provide chemical information of the tagged cells or organelles. Lacking such information hinders functional analysis, such as assessment of cell metabolic activity.

Providing chemical specificity, high-speed and high-sensitivity vibrational spectroscopic imaging is an emerging platform. Recently-developed coherent Raman scattering microscopy, based on coherent anti-Stokes Raman scattering (CARS) or stimulated Raman scattering (SRS), has allowed real-time vibrational imaging of biomolecules in living cells and tissues. Advanced instrumentation has pushed the stimulated Raman spectral acquisition speed to microsecond scale. Adoption of stable isotope probes and alkyne-based Raman tags greatly enhanced the detection sensitivity, specificity and functionality in SRS microscopy. Being highly sensitive to C—H vibrations, CARS and SRS imaging have unveiled new signatures of lipid metabolism in a variety of biological systems. In comparison, high-speed CARS or SRS imaging of fingerprint Raman bands remains difficult.

Mid-infrared spectroscopy is complementary to Raman spectroscopy. Unlike Raman scattering, the infrared absorption cross section in the fingerprint region is larger than in the high-wavenumber C—H vibrational region. Fourier transform infrared (FTIR) spectroscopy is one of the most extensively used techniques for chemical characterization and analysis of biological cells and tissues The inherent vibration absorption of mid-infrared photons by biological macromolecules including proteins, lipids, carbohydrates, and nucleic acids shows distinctive absorption bands. Shifts in relative heights of absorption bands, peak positions, and peak shape provide rich biomolecular information, including concentration, conformation, and orientation. FTIR spectroscopy has provided new insights in tissue classification drug and tissue interaction, neurodegenerative diseases, cancer progression, and so on. However, the spatial resolution of infrared spectroscopic imaging is limited by the long mid-infrared illumination wavelength, ranging from 5 to 20 Strong water absorption further hinders its application to living cells.

To overcome these limitations in infrared spectroscopy, a new platform, termed mid-infrared photothermal (MIP) microscopy, has been developed to reach sub-micron spatial resolution. The MIP effect relies on a photothermal process in which infrared absorption corresponds to a specific molecular vibrational bond causes a localized temperature rise at the vicinity of target molecules. This photothermal effect consequently induces a change of refractive index and a thermal expansion. The MIP signal is then obtained by probing these changes using a visible beam which provides a much smaller diffraction limit than the mid-infrared illumination, enabling a spatial resolution down to 300 nm. Following the first demonstration of MIP imaging of living cells, technical innovations have been made to enable MIP detection in wide-field, using scattering or phase signals. Meanwhile, MIP microscopy and its commercial product have found various applications in studying living cell, pharmaceuticals, viruses, and bacteria. Yet, the photothermal effect induces only a tiny change in intensity and angular distribution of the scattered probe light, due to the weak thermal dependence of particle size and refractive index. Typical fractional change is on the order of $10^{-4}$/K, set by the intrinsic thermal properties of most materials. Such small modulation depth limits the signal to noise ratio (SNR), especially in the wide-field mode where the probe beam intensity at each pixel is limited by the well depth of a CMOS camera.

Figure 7A:
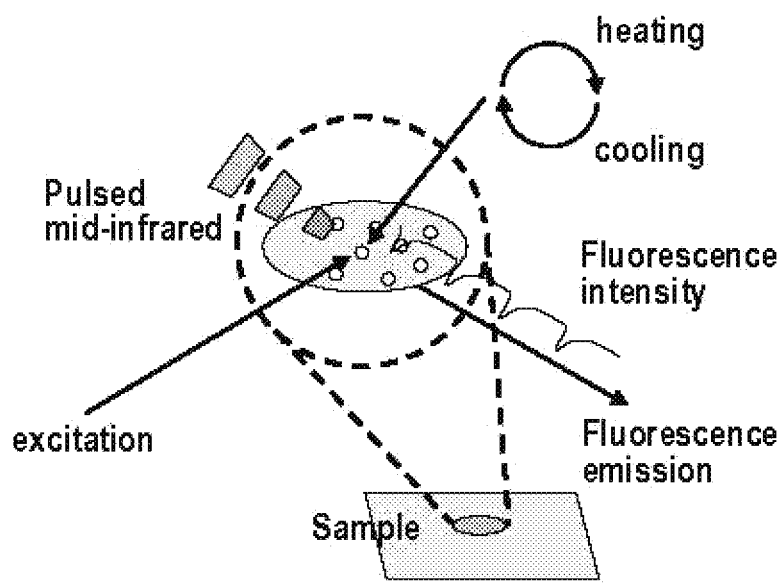
FIG. 7A includes a schematic diagram of a point scanning FE-MIP microscope, according to some exemplary embodiments.

According to the present disclosure, a fluorescence-detected MIP (F-MIP, also referred to herein as "FE-MIP") microscope, for example, microscope 100A of FIG. 2A and microscope 100B in FIG. 3A, that utilizes thermo-sensitive fluorescent dyes as probes of the photothermal effect is provided. The F-MIP principle is illustrated in FIG. 7A. Referring to FIGS. 1A and 7A, a sample 102 stained with a thermo-sensitive dye is heated upon IR absorption by targeted molecules. The infrared pulse train 104 heats the surroundings of the fluorescent probe and causes a temperature rise, which subsequently modulates the fluorescence emission efficiency. Such modulation is then measured by a lock-in amplifier, such as, for example, lock-in amplifier 136 illustrated in FIG. 2C. Using fluorescent dye to measure the temperature has been known. Yet, it has not been used as a probe for infrared spectroscopic imaging. The present technology provides important advantages over scattering-based MIP microscopy. One advantage is the utilization of much larger photothermal response of fluorescent dyes compared to scattering. Common fluorophores including FITC, Cy2, Cy3, Rhodamine, and green fluorescent protein have temperature-dependent emission efficiency on the order of 1%/K, which is nearly 100 times larger than scattering dependence on temperature. Thus, one can in principle boost the mid-infrared photothermal imaging speed by two orders of magnitude. As a second advantage, as fluorescence appears at a new wavelength from the incident beam, it is insensitive to the laser relative intensity noise. As a third advantage, unlike scattering, fluorescence is incoherent and thus does not generate interference patterns. As a fourth advantage, fluorescent probes can target specific cells, intracellular organelles, or specific molecules, thus offering an enhanced specificity beyond the reach by scattering-based MIP microscopy. In the present disclosure, two F-MIP systems are provided, one in a point-scanning mode, illustrated as system 100A in FIG. 2A, and one in a wide-field mode, as illustrated as system 100B in FIG. 3A, as described in detail herein.

Experimental Section

For an experiment with scanning F-MIP microscope 100A: A pulsed mid-IR pump beam is generated by a tunable (from 1000 to 1886 $cm^{-1}$) quantum cascade laser (QCL, Daylight Solutions, MIRcat-2400) operating at 100 kHz repetition rate and 900 ns pulse duration. The IR beam passes through a calcium fluoride ($CaF_2$) cover glass and is then focused onto a sample through a gold-coating reflective objective lens (52×; numerical aperture (NA), 0.65; Edmund Optics, #66589). A continuous-wave probe laser (Cobolt, Samba) at 532 nm is focused onto the same spot from the opposite side by a refractive objective (60×; NA, 1.2; water immersion; Olympus, UPlanSApo). The probe beam is aligned to be collinear to the mid-IR pump beam. The reflective objective is fine tuned in 3D to ensure overlap of the two foci. A scanning piezo stage (Mad City Labs, Nano-Bio 2200) with a maximum scanning speed of 200 μs/pixel is used to scan the sample. The fluorescence is collected by the same refractive objective, reflected by a dichroic mirror (Thorlabs, DMSP550R, 550 nm cutoff), filtered by a long-pass filter (Thorlabs, FEL0550, 550 nm cutoff), and then collected by a PMT (Hamamatsu, H10721-110). Specimens on a $CaF_2$ coverglass are first imaged by fluorescence. Then, the pulsed IR laser is turned on and the modulated fluorescence signal is collected by the same PMT. The F-MIP signal is extracted by a lock-in amplifier (Zurich Instruments, HF2LI). A laboratory-built resonant circuit is used to amplify the photocurrent from the PMT before it is sent to the lock-in. Before the reflective objective, the infrared laser passes through the $CaF_2$ slip and the reflected infrared laser intensity is measured by a mercury cadmium telluride (MCT) detector for normalization of IR power at each wavelength.

For an experiment with wide-field F-MIP microscope 100B: The IR pulses are generated by the same QCL used in scanning F-MW. The visible probe beam for fluorescence excitation (wavelength at 488 nm or 520 nm) is obtained by second-harmonic generation of a quasi-continuous femtosecond laser tuned to 976 nm or 1040 nm (Coherent Inc, Chameleon, 140 fs, 80 MHz). Prior to second-harmonic generation, the femtosecond beam is chopped into a 200-kHz pulse train (300 ns pulse width) by an acousto-optical modulator (AOM, Gooch and Housego). The IR beam passes through the substrate and is weakly focused onto a sample by a parabolic mirror (f=15 mm, Thorlabs, MPD00M9-M01). Using a Kohler illumination configuration, the probe beam is focused on the back focal plane of the objective lens (50×, 0.8 NA, Nikon) by a condenser (f=75 mm, AC254-075-A, Thorlabs). The fluorescence emission is collected by the same objective lens, and after a long pass filter, collected by a CMOS camera (FLIR, Grasshopper3 GS3-U3-51S5M). The F-MIP images are acquired by a virtual lock-in camera approach. Briefly, a pulse generator (Emerald Pulse Generator, 9254-TZ50-US, Quantum Composers) generates a master clock signal at 200 kHz and externally triggers the QCL, the AOM and the CMOS camera to synchronize the IR pump pulses, the probe pulses, and camera exposure. The schematic is shown in FIG. 3A.

Cancer cell culture and staining: Mia Paca2 cells were purchased from the American Type Culture Collection (ATCC). The cells were cultured in RPMI 1640 medium supplemented with 10% FBS and 1% P/S. All cells were maintained at 37° C. in a humidified incubator with 5% $CO_2$ supply. For Nile red staining, cells were incubated with 10 μM Nile Red (Invitrogen) for 30 minutes at room temperature followed with 15 minutes fixation in 10% neutral buffered formalin. For rhodamine 123 (Invitrogen) staining, cells were incubated with 10 μg/ml rhodamine 123 for 30 minutes at 37° C.

Bacterial culture and staining: *Staphylococcus aureus* (*S. aureus*) was incubated in a MHB medium for 10 h. After centrifuging and washing in phosphate-buffered saline (PBS), the bacteria were fixed by formalin solution for 0.5 h. Rhodamine 6G or Cy2 at $10^4$ M was then added into the bacteria pellet. The pellet was then resuspended and incubated for 1 h. With final washing steps, 2 μL sample were dried on a $CaF_2$ coverslip for imaging. *Shigella flexneri* expressing GFP was grown overnight at 37° C. on a tryptic soy agar plate. Colonies with green fluorescence were picked up by sterile inoculation loops and then resuspended in PBS. The bacterial solution was diluted by optical density at 600 nm (OD600) to 0.1. The bacteria were then fixed by 10% Formalin for 30 min at room temperature. The bacteria solution was washed twice by PBS before imaging.

Figure 7B:
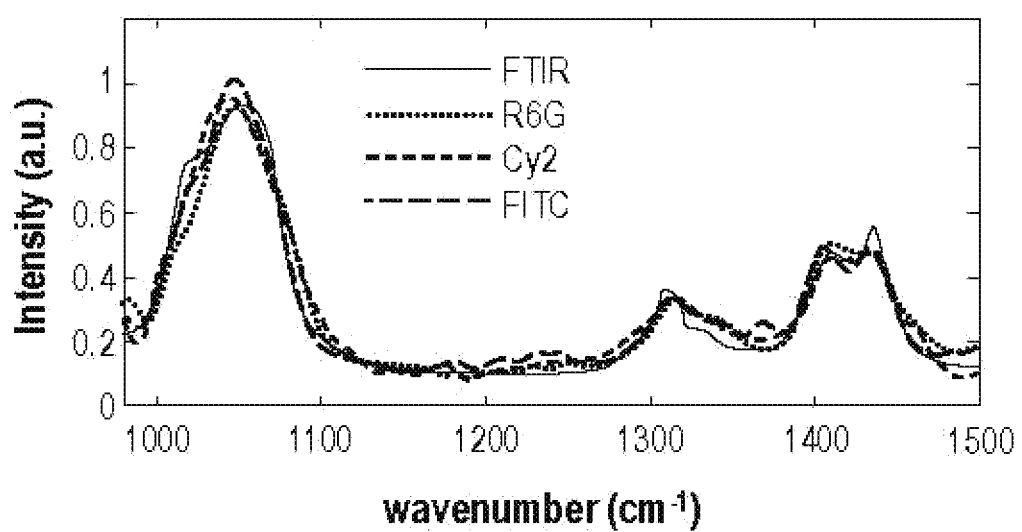
FIG. 7B illustrates F-MIP spectra of DMSO supplemented with various thermo-sensitive fluorescent dyes.

FIG. 7A illustrates the fluorescence-detected mid-infrared photothermal (F-MIP) sensing approach, using point scanning microscope 100A, and spectral fidelity. Referring to FIG. 7A, modulation of fluorophore emission intensity by pulsed infrared pump of surrounding molecules is illustrated. As described above in detail FIG. 2A illustrates the schematic of point scanning F-MIP microscope 100A. A pulsed mid-IR pump beam from a quantum cascade laser (QCL) and a continuous visible fluorescence excitation beam are focused at the sample with a reflective objective and a water-immersion objective, respectively. The fluorescence emission is reflected by a dichroic mirror (DM), filtered and directed to a photomultiplier tube (PMT). A beam splitter is placed to reflect the scattered visible beam to a photodiode for scattering-based MIP (Sc-MW) imaging. FIG. 2C illustrates the electronics connections. The photothermal signal is detected by a PMT connected to a resonant amplifier (RA) and detected by a lock-in amplifier. A PC is used for controlling the scanning stage and data acquisition. FIG. 7B illustrates F-MIP spectra of DMSO supplemented with various thermo-sensitive fluorescent dyes. For each dye, standard deviation of three independent measurements is shown at each wavenumber. The FTIR spectrum of DMSO (black) is shown for comparison.

Results and Discussion

Point-Scanning F-MIP Microscope 100A and Spectral Fidelity

Based on the principle illustrated in FIG. 7A, we have built a scanning F-MIP microscope as shown in FIG. 2B. A QCL laser provides IR pulses tunable in the entire fingerprint region. The repetition rate and pulse width were set to be 100 kHz and 900 nanoseconds, respectively. Two CW lasers at 532 nm and 488 nm were used for fluorescence excitation. The fluorescence was detected by a photomultiplier tube and the F-MW signal was extracted by a lock-in amplifier. On the same setup, a photodiode was also installed for scattering-based MIP (Sc-MIP) imaging using the 532-nm laser as the probe beam. The electronics connections are shown in FIG. 2C.

Using this system, we have validated the spectral fidelity of F-MW microscope 100A. We dissolved various thermo-sensitive dyes in DMSO, at 100 µM concentration. We then recorded the F-MIP signals while scanning the QCL laser. At each wavenumber, the F-MIP intensity was normalized by the IR intensity measured by MCT. In all cases (FIG. 7B), the F-MW spectra show the same peak intensity and width as the FITR spectrum of DMSO. Importantly, because the dye concentration (100 µM) is much lower than DMSO concentration (14 M), the dyes do not interfere with the F-MIP spectra. These data demonstrate the F-MIP microscope is able to produce reliable spectral information.

Figure 8A:
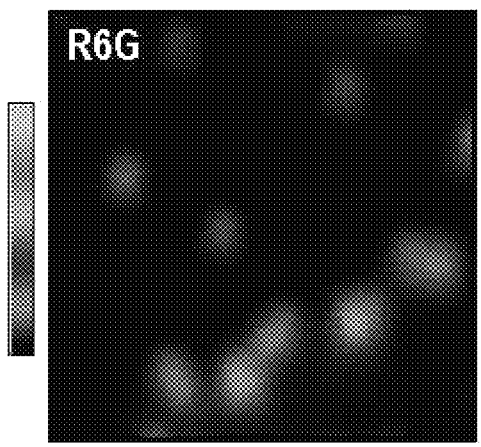
FIGS. 8A through 8G illustrate F-MIP imaging and fingerprinting single S. aureus.
Figure 8B:
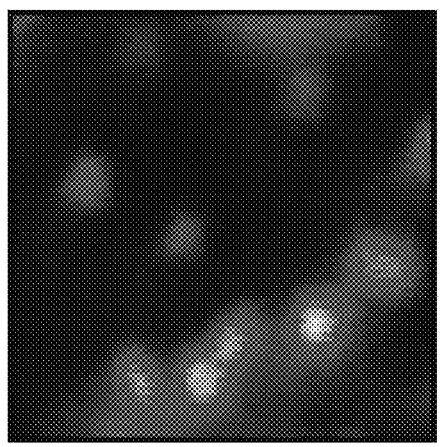
Figure 8C:
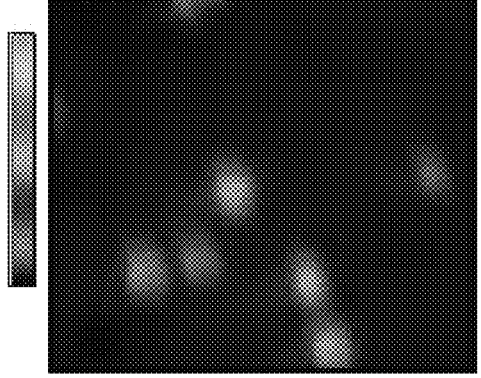
Figure 8D:
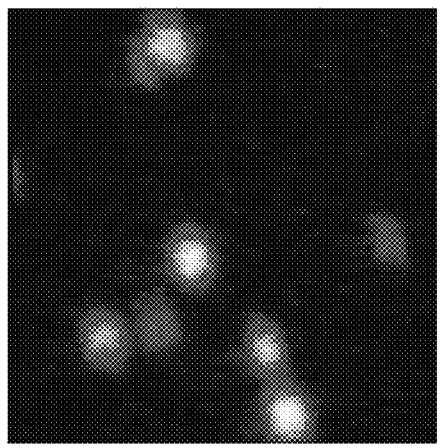
Figure 8E:
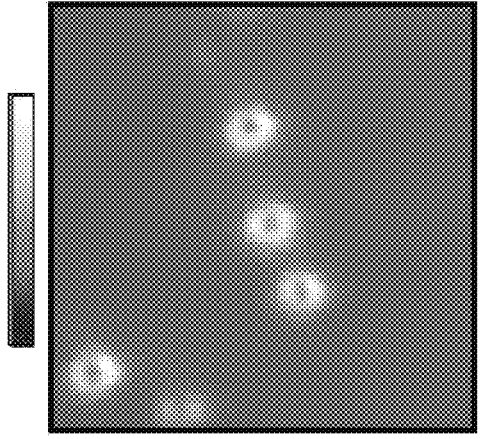
Figure 8F:
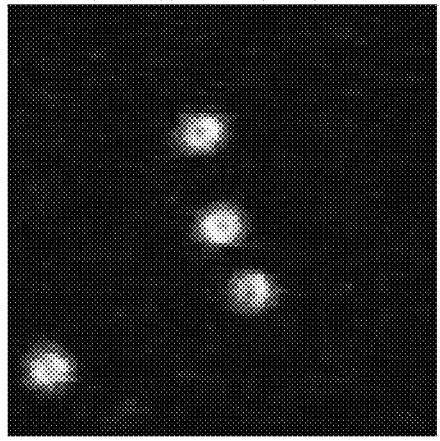
Figure 8G:
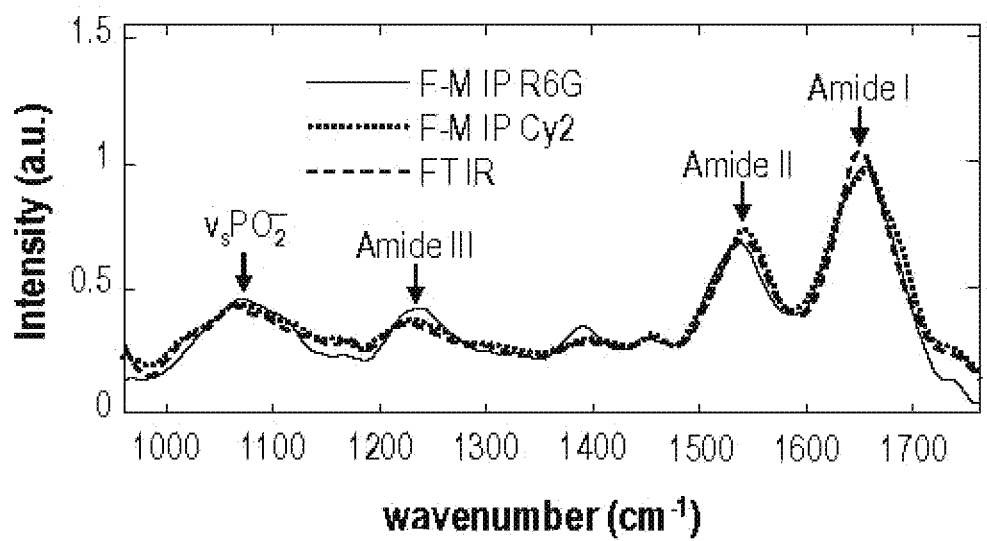

FIGS. 8A through 8G illustrate F-MW imaging and fingerprinting single S. aureus. FIG. 8A illustrates fluorescence image of S. aureus stained with R6G. Scale bar: 1 µm. Pixel dwell time: 1 ms. Fluorescence excitation: 0.025 mW at 532 nm. FIG. 8B illustrates F-MIP image of same S. aureus at 1650 cm$^{-1}$. FIG. 8C illustrates fluorescence image of S. aureus stained with Cy2. Fluorescence excitation: 0.025 mW at 488 nm. FIG. 8D illustrates F-MIP image of same S. aureus at 1650 cm$^{-1}$. FIG. 8E illustrates scattering image of S. aureus. Pixel dwell time: 1 ms. Visible probe power: 1.5 mW. FIG. 8F illustrates Sc-MIP image of same S. aureus at 1650 cm$^{-1}$. FIG. 8G illustrates the fingerprint spectra of S. aureus measured by F-MW and Sc-MW, respectively. For both F-MW and Sc-MW, the IR laser power 1650 cm$^{-1}$ was 10.2 mW at sample. The FTIR spectrum recorded from a film of dried S. aureus was adopted from Li, X.; Zhang, D.; Bai, Y.; Wang, W.; Liang, J.; Cheng, J.-X., "Fingerprinting a living cell by Raman integrated mid-infrared photothermal microscopy," Analytical Chemistry 2019, 91 (16), 10750-10756.

F-MIP Imaging and Fingerprinting of Single Bacteria

We applied the F-MIP microscope 100A to image single S. aureus bacteria to evaluate its chemical imaging capability on biological specimens (FIGS. 8A-8D). The S. aureus culture was diluted to a concentration of around 5×10$^5$/mL and then dried on a CaF$_2$ substrate. The S. aureus particles were stained with fluorescence dye Cy2 and R6G, respectively. For each specimen, we acquired fluorescence and F-MIP images of the same bacteria at 1650 cm$^{-1}$ targeting the amide I band. For the F-MW images, SNRs of 26 and 34 were achieved for R6G and Cy2 labeled bacteria at the fluorescence excitation power of 0.025 mW at the sample. For comparison, we recorded scattering and MIP images of the same specimen (FIGS. 8E-8F). In order to obtain a similar SNR of 37, an excitation power of 1.5 mW at sample was required, which is 60 times of the probe power used for F-MIP. On a single bacterium, we recorded the vibrational fingerprint spectrum (FIG. 8G). The F-MIP spectra based on R6G and Cy2 matches well the FTIR spectrum, showing distinct peaks at 1650, 1550, and 1080 cm$^{-1}$ for protein amide I, protein amide II, and nuclei acid phosphate vibrations, respectively. This comparison demonstrates the spectral fidelity of F-MIP in single bacterium analysis. Notably, the scattering and the Sc-MIP image both show a ring structure, with bright contrast from the peripheral of the cell (FIGS. 8E-8F), whereas the F-MIP images (FIGS. 8B, 8D) show bright contrast from the entire cell. This result indicates that F-MIP is immune to edge-enhanced back scattering from a sizable particle.

Figure 9A:
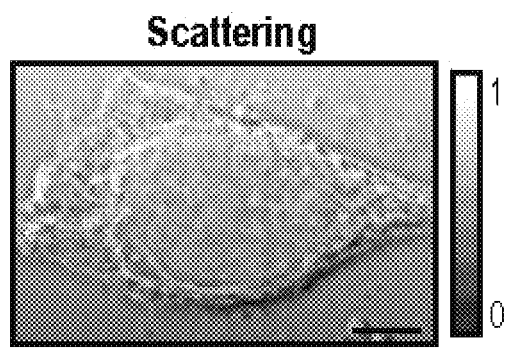
FIGS. 9A though 9I illustrate Sc-MIP and F-MIP images of living MiaPaca2 cancer cells.
Figure 9B:
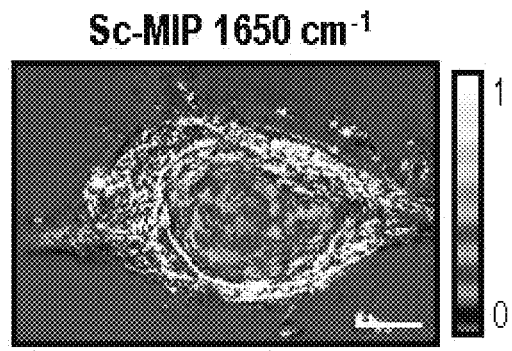
Figure 9C:
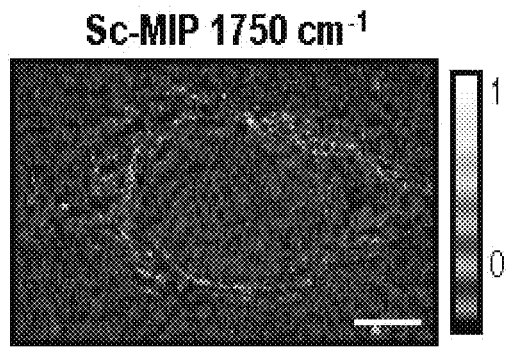
Figure 9D:
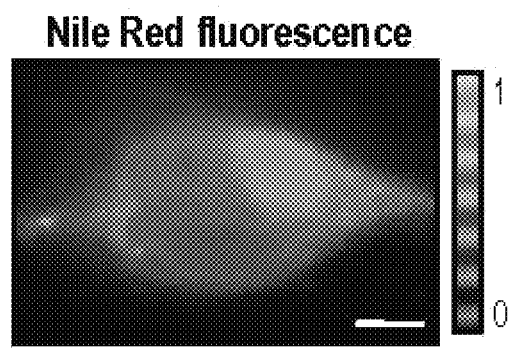
Figure 9E:
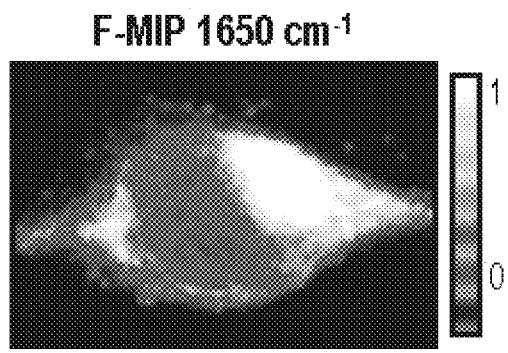
Figure 9F:
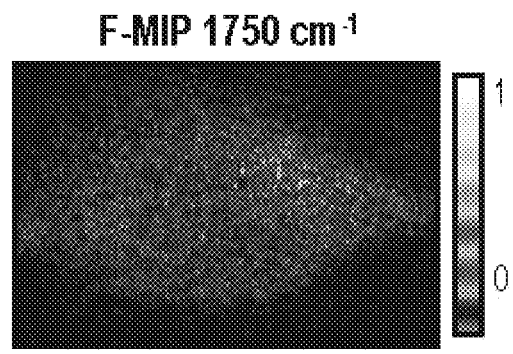
Figure 9G:
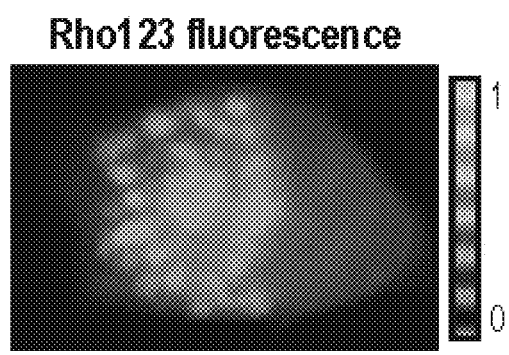
Figure 9H:
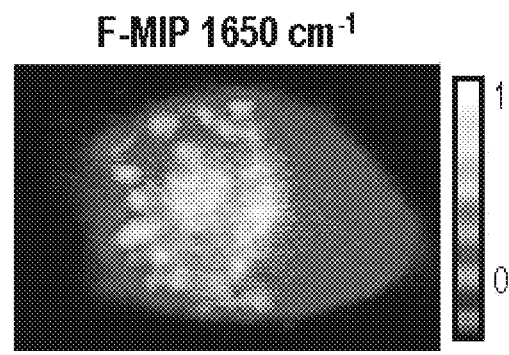
Figure 9I:
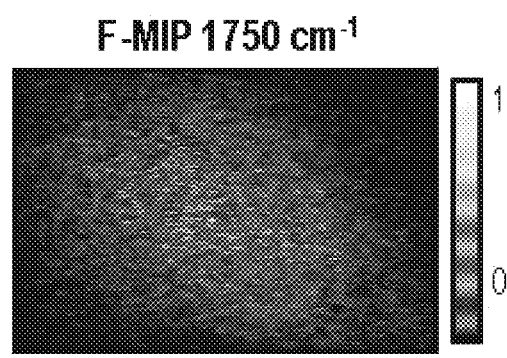

FIGS. 9A though 9I illustrate Sc-MIP and F-MIP images of living MiaPaca2 cancer cells. FIG. 9A illustrates scattering image of a MiaPaca2 cell. FIG. 9B illustrates Sc-MIP image of the same cell at 1650 cm$^{-1}$. FIG. 9C illustrates Sc-MIP image at 1750 cm$^{-1}$. FIG. 9D illustrates a fluorescence image of the same MiaPaca2 cell stained with Nile red. The probe laser is at 532 nm. FIG. 9E illustrates F-MIP image at 1650 cm$^{-1}$. FIG. 9F illustrates F-MIP image at 1750 cm$^{-1}$. FIG. 9G illustrates fluorescence image of a different MiaPaca2 cell stained with Rhodamine 123 (Rho123). The probe laser is at 488 nm. FIG. 9H illustrates F-MW image at 1650 cm$^{-1}$. FIG. 9I illustrates F-MW image at 1750 cm$^{-1}$. Scale bar: 5 µm.

Sc-MW and F-MIP Imaging of Cancer Cells

Compared to bacteria, eukaryotic cells contain a nucleus and highly organized organelles in the cytoplasm. In the transmission image shown in FIG. 9A, the scattering-based contrast shows the overall cell morphology. Accordingly, the Sc-MIP image (FIG. 9B) at 1650 cm$^{-1}$ corresponding to the amide I band shows the protein content inside the nucleus and protein-rich structures in the cytoplasm, without specificity to a certain organelle. The contrast decreases when the IR laser is tuned to 1750 cm$^{-1}$ (FIG. 9C), showing the chemical specificity. In contrast, fluorescence microscopy is able to visualize specific biomolecules and/or intracellular organelles via the versatile fluorescent probes. For instance, Nile red can selectively stain the intracellular lipid droplets and membranes while Rhodamine 123 is a specific probe for localizing mitochondria in living cells. By staining the same cell with Nile red and excitation of the dye at 532 nm, phospholipid membranes in the cell are visualized (FIG. 9D), where the brightest contrast is likely from the ER membrane. The F-MIP image at 1650 cm$^{-1}$ gives the distribution of proteins in areas labeled by Nile red (FIG. 9E). The contrast nearly disappears when the IR laser is tuned to 1750 cm$^{-1}$ (FIG. 9F), showing the chemical specificity. To show that our method is applicable to other dyes, we performed an independent experiment in which living MiaPaca2 cells were labeled by Rhodamine 123 targeting intracellular mitochondria (FIG. 9G). In accordance, the F-MIP image at 1650 cm$^{-1}$ shows selective and bright contrast from the Rhodamine 123 labeled region (FIG. 9H) and the contrast disappears at 1750 cm$^{-1}$ (FIG. 9I).

From Point-Scanning to Wide-Field F-MIP

In the above experiments, the power used for F-MIP imaging is at the microwatt level and is 60 times less than the power used for scattering MIP imaging. The extremely low photon budget for F-MIP imaging opens the opportunity of increasing the throughput via wide-field illumination with IR pump pulses and visible probe pulses. Importantly, compared to scanning F-MW, wide-field F-MW significantly reduces the fluorophore photobleaching rate based on the following consideration. In the experiment, the IR pulse is 900 ns in duration and the pulse-to-pulse duration is 10 μs. In the aqueous environment, the temperature profile largely follows the IR pulse. Thus, in a scanning experiment where a continuous wave probe laser is used, the duty cycle is about 10%. Yet, in a wide field measurement, only two visible pulses are needed to measure the IR-on and IR-off states. Thus, the duty cycle can be 50%. In this way, the probe laser power can be significantly reduced, thus alleviating the photobleaching issue. Notably, our group recently demonstrated scattering-based wide-field MIP imaging. Yet, the signal-to-noise ratio at the high-speed mode is limited by the weak dependence of scattering on temperature and the small well depth of the CMOS camera. As a result, a large number of integrations were needed to accumulate sufficient photons to probe the MIP signal. Unlike the scattering photons, the fluorescence usually does not saturate the camera. Due to the high thermo-sensitivity of fluorescent probes, it is anticipated that the MIP signal can be extracted from two sequential frames (hot and cold) without further average.

Wide Field F-MIP Imaging System

Figure 10A:
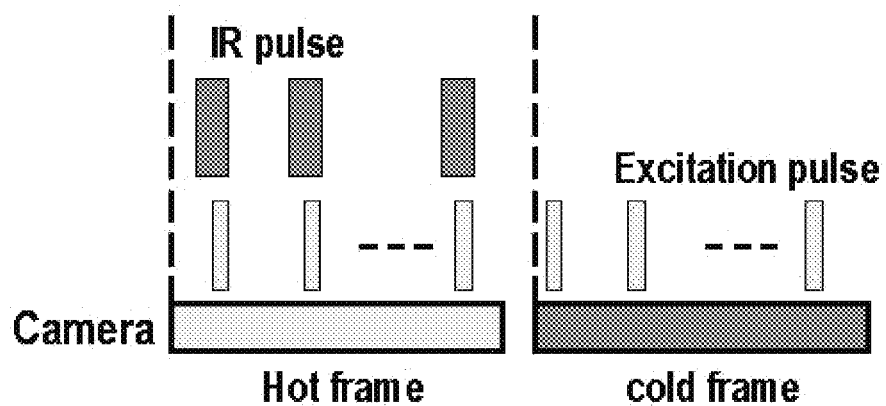
FIG. 10A illustrates temporal synchronization of the IR pump pulse, fluorescence excitation pulse, and camera exposure.
Figure 10B:
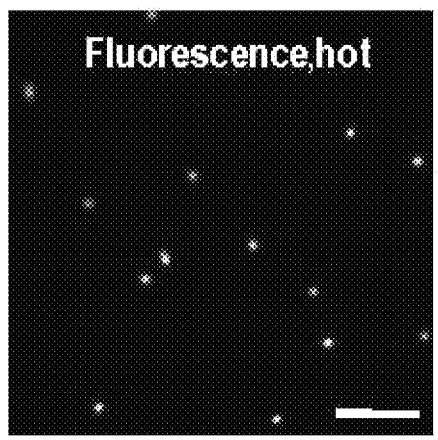
FIGS. 10B and 10C illustrate a wide field fluorescence image of Cy2-stained S. aureus with IR on and IR off, designated as hot and cold, respectively.
Figure 10C:
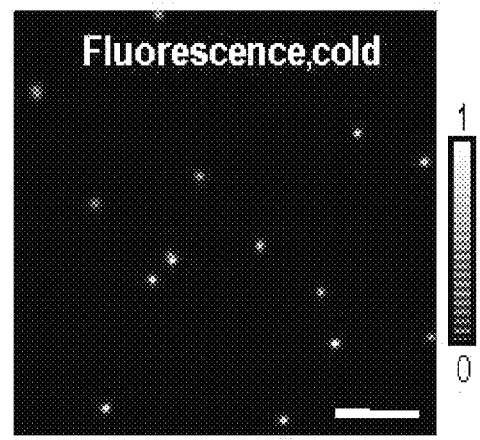
Figure 10D:
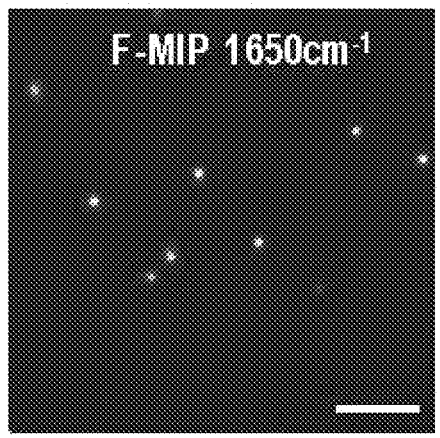
FIG. 10D illustrates wide field F-MW at 1650 cm$^{-1}$.
Figure 10E:
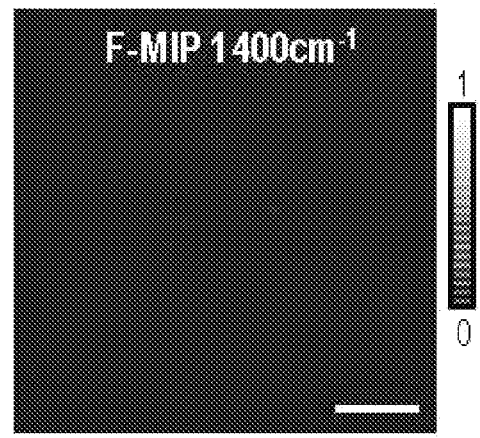
FIG. 10E illustrates F-MIP at 1400 cm$^{-1}$ off resonance.

As described above in detail, FIG. 3A illustrates the wide field F-MIP microscope 100B of exemplary embodiments. The infrared laser generated by the QCL 160 is focused by a parabolic mirror. The visible light modulated by AOM 162 illuminates the sample and excites the fluorescence. The fluorescence is filtered and collected by CMOS camera 164. FIG. 10A illustrates temporal synchronization of the IR pump pulse, fluorescence excitation pulse, and camera exposure. FIGS. 10B and 10C illustrate a wide field fluorescence image of Cy2-stained S. aureus with IR on and IR off, designated as hot and cold, respectively. FIG. 10D illustrates wide field F-MIP at 1650 cm$^{-1}$, and FIG. 10E illustrates F-MIP at 1400 cm$^{-1}$ off resonance. Scale bar: 10 μm. Fluorescence excitation: 488 nm, 1 mW. IR pulse rate: 200 KHz. Camera frame rate: 40 Hz.

In wide-field F-MIP microscope 100B shown in FIG. 3A, the pulsed infrared laser is weakly focused onto a sample by a parabolic mirror. An 80-MHz femtosecond laser is modulated by an AOM and frequency-doubled to visible window. The broad bandwidth of femtosecond pulses reduces speckles in scattering-based MIP imaging. The virtual lock-in detection scheme is illustrated in FIG. 10A. The fluorescence excitation pulse is synchronized with the IR pump pulse. In the cold frame, no IR pump pulses heat the sample. The camera detects the hot and cold frames sequentially at an exemplary 40 Hz frame rate. The difference (cold–hot) generates the MIP image. The average probe laser power is approximately 1 mW and the exposure time is approximately 300 ns. The IR power is in the range from 5 to 15 mW depending on the spectral window examined. To characterize the spatial resolution, we mapped Cy2-label polystyrene beads with diameter of 500 nm, the F-MIP intensity profile shows a full-width at half maxim of 610 nm. After deconvolution with particle size, the spatial resolution is estimated to be 390 nm, which is close to the diffraction limit of the 0.8 NA objective.

To demonstrate the applicability of wide-field F-MIP to biological specimens, we deposited S. aureus stained with Cy2 onto a silicon substrate and measured the fluorescence with IR on and IR off sequentially. The hot frame and the cold frame are illustrated in FIGS. 10B and 10C, respectively. By subtracting the hot from the cold frame, the intensity difference generates the F-MIP image shown in FIG. 10D. When the IR laser is tuned to 1650 cm$^{-1}$, corresponding to the amide I band of proteins, a signal to noise ratio of 30 was obtained. The IR pulse only heats the upper half of the field of view. For this reason, only the S. aureus particles in the upper part give the F-MIP contrast. When the IR laser is tuned to 1400 cm$^{-1}$, off resonance to major IR peaks, the contrast nearly disappears, as illustrated in FIG. 10E. It is noted that the wide-field F-MW imaging speed of 20 frames per second is 2000 times faster than the scanning F-MW imaging speed (100 seconds per frame with a pixel dwell time of 1.0 millisecond).

Performance Comparison Between Wide-Field Sc-MW and F-MIP

FIGS. 11A-11N illustrate performance comparison between wide field SC-MIP and wide field F-MIP systems. FIG. 11A illustrates a fluorescence image of S. aureus deposited on a silicon substrate. FIG. 11B illustrates a single frame F-MIP image of the same cells at 20 Hz speed. FIG. 11C illustrates F-MIP image of the same cells with 100 frames average. FIG. 11D illustrates a scattering image of S. aureus deposited on a silicon substrate. FIG. 11E illustrates a single frame Sc-MIP of the same cells shown in panel d at 20 Hz speed. FIG. 11F illustrates Sc-MIP of the same field of view with 100 frames average. FIG. 11G illustrates intensity profile along the white line marked in FIGS. 11B and 11E. FIG. 11H illustrates intensity profile along the white line marked in FIGS. 11C and 11F. FIG. 11I illustrates fluorescence intensity of single S. aureus in sequentially acquired hot and cold frames. FIG. 11J illustrates scattering intensity of single S. aureus in sequentially acquired hot and cold frames. The IR laser is tuned to 1650 cm$^{-1}$ for data in FIGS. 11A-11K. FIG. 11K illustrates fluorescence image of Sheila flexneri bacteria expressing GFP. FIG. 11L illustrates a single frame F-MIP of the same bacteria at 1650 cm$^{-1}$. FIG. 11M illustrates a F-MIP image of the same field of view with 100 frames average. FIG. 11N illustrates fluorescence intensity of the square area in sequentially acquired hot and cold frames.

The performance of fluorescence-enhanced and scattering-based MIP imaging in the wide field mode were compared, using S. aureus on a silicon substrate as testbed. FIGS. 11A-11C illustrate the fluorescence and F-MIP images of individual S. aureus with the IR laser tuned to 1650 cm$^{-1}$. The signal to noise ratio for a single bacterium reaches 33 in single frame F-MIP and 275 after 100 frames average. FIGS. 11D-11F illustrate the scattering and SC-MIP images of individual S. aureus with the IR laser tuned to 1650 cm$^{-1}$. FIGS. 11G-11H illustrate the intensity profile across the white line indicated in the images. The Sc-MIP contrast is completely buried in the speckle pattern in singe frame acquisition. After 100 frames average, the signal to noise ratio reaches 14, which is 20 times lower than F-MIP of the same sample. The much higher signal to noise ratio in F-MW can be attributed to the lack of shot noise from scattered photons and the much larger thermo-sensitivity of the fluorescence probe. FIG. 11H shows similar line width for the bacterium in Sc-MW and F-MW. However, the F-MIP intensity does not suffer from the interference (i.e. the dark ring around the peak) encountered in the Sc-MIP image. FIGS. 11I-11J illustrate the F-MW and Sc-MW intensities from a single bacterium in sequentially acquired hot and cold frames. The modulation depth, defined as percentage of intensity difference between hot and cold frames, is found to be about 4% for F-MW, but is buried in frame-to-frame fluctuations in Sc-MIP. Moreover, FIG. 11I shows negligible photobleaching in the recorded 50 frames over a period of 1.25 seconds.

Besides fluorescent dyes, the feasibility of F-MW imaging for cells expressing green fluorescent proteins (GFPs) was tested. It has been shown that GFPs are highly thermo-sensitive with 1% intensity decrease per degree in temperature rise. Accordingly, in F-MIP imaging of *Sheila flexneri* bacteria expressing GFP (FIGS. 11K-11M), 2% fluorescence intensity difference between cold and hot frames was observed (FIG. 11N). The signal-to-noise ratio reaches 10 and 97 in single frame and 100 frames average, respectively. The recorded 50 frames only experienced 3% photobleaching. The fluorescence fluctuation from frame to frame was due to laser instability.

Photothermal microscopy is a pump-probe technique involving modulation of the pump beam and demodulation of the signal usually by a lock-in. In the present disclosure, the sensitivity is defined as the modulation depth, $\Delta I_{pr}/I_{pr}=\sigma I_p$, where $\sigma$ is related to the thermal sensitivity, $I_p$ is the IR pump, and $I_{pr}$ is the probe intensity. In this sense, fluorescence-detected MIP is more sensitive than scattering-based MIP due to the much larger thermo-sensitivity of fluorophores. Experimentally, as shown in FIGS. 11A-11N, the modulation depth in F-MIP is about 2%, whereas the modulation is buried in frame-to-frame intensity fluctuation in Sc-MIP.

We have defined the imaging SNR as the ratio of signal intensity from single particles to pixel-to-pixel background fluctuations. Thus, in Sc-MW, the SNR=Signal/(Noise_PD+Noise_photon). In SNR=Signal/Noise_PMT. Under the shot noise limit, the photon noise is proportional to $\sqrt{I_{pr}}$. Based on this model, the SNR depends on the value of a and the probe beam intensity if we assume that same IR pump beam is used. In scanning MW microscopy, the probe power (~10 mW) in the scattering mode can be 10,000 times larger than that in the fluorescence mode (~1 μW). In this case, the SNR in Sc-MIP is dominated by the photon noise, and the SNR=$\alpha_{sc} I_p \sqrt{I_{pr}}$. In F-MIP, the SNR=$\sigma_f I_p I_{pr}$/Noise_PMT. In this case, the SNR in F-MIP is a trade-off between a much larger a and a much smaller $I_{pr}$ used. Experimentally, we observed similar SNR in F-MIP compared to Sc-MW (See FIGS. 8A-8G). However, in wide-field MIP microscopy, limited by the well depth of a common CMOS camera, the probe power at each pixel is at the nW level for both the scattering and the fluorescence modality. In this case, the detector noises dominate, and the SNR in F-MIP can be theoretically larger by two orders of magnitude than that in Sc-MIP. In the experiment, we showed that the SNR in wide-field MIP is 20 times larger than that in wide-field Sc-MIP.

Theoretically, F-MW microscopy is based the thermal diffusion from the target molecule to the fluorescent probe. The thermal diffusion length is defined as $\mu_t=2\sqrt{\alpha t}$, where a is the thermal diffusivity. In an aqueous environment, the value of α is $1.4\times10^{-7}$ m$^2$/s. In our wide-field F-MIP experiment, the IR pulse is 900 ns in duration and the fluorescence excitation pulse is 300 nm. If we set the pump-probe delay to be 900 ns, the thermal diffusion length is ~700 nm, which is slightly larger than the diffraction limit of the visible probe beam. If one can use IR pump and visible probe pulse of 5 ns duration and the pump-probe delay is set to be 5 ns, the thermal diffusion length can be reduced to 50 nm. In this case, one can detect the chemical content surrounding the fluorescence probe on the nanoscale. If the probe is conjugated to the target molecule, like a GFP conjugated to a protein, the intramolecular vibrational redistribution on the picosecond scale can be much faster than inter-molecular vibrational redistribution. In principle, it could create an intramolecular F-MIP signal, assuming that picosecond IR pump and probe pulses are used.

The dependence of thermo-sensitivity on two important environmental factors, salt concentration and viscosity, has been previously studied. It was shown that thermo-sensitivity is nearly independent of salt concentration in the 10 to 100 mM range. Also, it was shown that PEG BODIPY lifetime in cells is due to temperature and independent of changes in viscosity. These data suggest that fluorophores' thermo-sensitivity can be used as a reliable readout of the mid-infrared photothermal effect.

F-MIP microscopy opens new opportunities for live-cell chemical imaging. First, F-MIP greatly enhances the specificity of MIP microscopy. To illustrate this advantage, one could normalize the F-MIP signal with the direct fluorescence signal. As shown in FIGS. 12A-12F, the normalized F-MIPs images exhibit a more uniform distribution of the signal arising from proteins in regions labeled by the dyes. In contrast, individual mitochondria are clearly seen in the F-MIP image (FIG. 9H) due to enrichment of rhodamine 123 in the mitochondria. Second, by F-MW spectroscopic imaging of specific organelles (e.g. lipid droplets) specifically labeled by a thermo-sensitive fluorophore (e.g. BODIPY), one will be able to tell not only the amount and distribution, but also the composition of lipids, which is beyond the reach by fluorescence microscopy alone. Such capacity will allow quantitation of lipid metabolism in cells under various conditions (e.g., in response to a stress). Third, F-MIP microscopy opens new ways to push the boundary of mid-infrared photothermal microscopy. For example, integration of infrared laser excitation and light field fluorescence probing is expected to enable single-shot volumetric infrared spectroscopic imaging at sub-micron spatial resolution. Additionally, structured illumination can be harnessed to break the diffraction limit of the visible beam, which is expected to push the spatial resolution of MIP microscopy to a new level.

Compared to MIP microscopy, F-MIP microscopy relies on labeling the specimen with a thermo-sensitive dye and the signal level depends on the dye concentration. Unlike scattering-based MIP, F-MIP cannot detect vibrational excitation at locations where fluorescent dyes do not exist. When interpreting the F-MW contrast, one should use the fluorescence image as a reference. For quantitative comparison of F-MIP signal level between different particles, normalization with fluorescence intensity is needed. An alternative approach is to measure the thermal modulation of fluorescence lifetime instead of intensity. For the same reason, the SNR in F-MW microscopy depends on the number of fluorophores in the particles to be detected. For biological nanoparticles such as virion particles, the small number of fluorescent labels may give a low signal level and limit the SNR accordingly. In such case, detection of interferometric scattering becomes a more suitable approach. In fact, detection and fingerprinting of single virus particles has been achieved by an interferometric mid-infrared photothermal microscope.

CONCLUSIONS

In efforts to push the detection limit and increase the specificity of optically detected mid-infrared photothermal microscopy, a new platform termed fluorescence-enhanced mid-infrared photothermal (F-MW) microscopy is developed. Our platform harnesses thermo-sensitive fluorescent probes to sense surrounding temperature rise induced by pulsed infrared excitation. High spectral fidelity is demonstrated for fluorescent probes in DMSO solution and inside biological cells. In the point scanning modality, we have demonstrated F-MIP imaging and fingerprinting of a single bacterium. While using fluorescence as a read out, the fingerprint information would allow functional assessment of biological specimen, such as metabolic response of bacteria to antibiotics treatment. Furthermore, organelle-specific F-MIP imaging is achieved, which opens exciting opportunities of probing the chemical content of intracellular organelles. In the wide-field modality, we demonstrated video rate, high signal to noise ratio, speckle-free F-MW imaging of individual bacteria. Finally, our platform is applicable to biological cells expressing GFP. This approach opens new opportunities of monitoring secondary structure of specific proteins tagged by GFP, which is beyond the reach by IR spectroscopy or fluorescence spectroscopy alone.

Whereas many alterations and modifications of the disclosure will become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A method for infrared microscopic analysis of a sample, comprising:
    a) labeling the sample with at least one fluorophore to create a fluorescently-labeled sample;
    b) directing a beam of mid-infrared radiation onto at least a portion of the fluorescently-labeled sample;
    c) directing an optical probe beam to impinge on the fluorescently-labeled sample at least partially overlapping with the mid-infrared radiation, wherein the optical probe beam provides optical excitation of the fluorescently-labeled sample;
    d) detecting fluorescent emissions from the fluorescently-labeled sample;
    e) detecting changes in the fluorescent emissions from the fluorescently-labeled sample due to absorption of the mid-infrared radiation by the fluorescently-labeled sample; and
    f) obtaining a signal indicative of infrared absorption by the fluorescently-labeled sample resulting from changes in fluorescent emission by the portion of the fluorescently-labeled sample due to temperature-dependent fluorescent emission of the at least one fluorophore.

2. The method of claim 1, wherein the fluorescently-labeled sample comprises a sample labeled with a fluorescent dye comprising at least one of rhodamine B, fluorescein, cy2, cy3, Nile red and green fluorescent protein.

3. The method of claim 1, further comprising pulse modulating the mid-infrared beam such that the mid-infrared beam is a pulse-modulated beam.

4. The method of claim 3, wherein a pulse repetition frequency of pulses in the mid-infrared beam is in a range of 1.0 to 1,000 kHz.

5. The method of claim 3, wherein a pulse repetition frequency of pulses in the mid-infrared beam is nominally 100 kHz.

6. The method of claim 3, wherein an on-time of a pulse of the mid-infrared beam is in a range of 1 nanosecond to 1 millisecond.

7. The method of claim 3, wherein a duty cycle of the mid-infrared beam is in a range of 0.01% to 50%.

8. The method of claim 1, further comprising scanning the mid-infrared beam over a plurality of portions of the fluorescently-labeled sample such that the image is generated for a plurality of portions of the fluorescently-labeled sample.

9. The method of claim 1, wherein:
    the mid-infrared beam is directed onto a plurality of portions of the fluorescently-labeled sample; and
    detecting fluorescent emissions from the sample when the probe beam impinges on the fluorescently-labeled sample is performed by a detector which comprises a two-dimensional array of detectors such that the image is generated for the plurality of portions of the fluorescently-labeled sample.

10. The method of claim 9, wherein the detector comprises a camera.

11. The method of claim 1, further comprising focusing the mid-infrared beam onto the sample with an objective.

* * * * *